US012060345B2

(12) United States Patent
Ryu et al.

(10) Patent No.: US 12,060,345 B2
(45) Date of Patent: Aug. 13, 2024

(54) PROCESS FOR PREPARING A PHTHALAZINONE DERIVATIVE AND INTERMEDIATES THEREOF

(71) Applicant: IDIENCE CO., LTD., Seoul (KR)

(72) Inventors: Keuncheol Ryu, Seoul (KR); Seoktaek Lee, Seoul (KR); Hanna Seo, Seoul (KR); Hyeran Yang, Seoul (KR); Wonje Seong, Seoul (KR); Jinyoung Yoon, Seoul (KR)

(73) Assignee: IDIENCE CO., LTD., Seoul (KR)

( * ) Notice: Subject to any disclaimer, the term of this patent is extended or adjusted under 35 U.S.C. 154(b) by 173 days.

(21) Appl. No.: 16/858,257

(22) Filed: Apr. 24, 2020

(65) Prior Publication Data
US 2021/0323946 A1   Oct. 21, 2021

Related U.S. Application Data

(60) Provisional application No. 63/013,310, filed on Apr. 21, 2020.

(51) Int. Cl.
*C07D 403/10* (2006.01)
(52) U.S. Cl.
CPC ................... *C07D 403/10* (2013.01)
(58) Field of Classification Search
CPC ............... C07D 403/10; C07D 205/04
See application file for complete search history.

(56) References Cited

U.S. PATENT DOCUMENTS

| | | | |
|---|---|---|---|
| 7,834,015 | B2 | 11/2010 | Jones et al. |
| 8,129,380 | B2 | 3/2012 | Menear et al. |
| 8,188,084 | B2 | 5/2012 | Jones et al. |
| 9,187,430 | B2 | 11/2015 | Ji et al. |
| 9,682,973 | B2 | 6/2017 | Kang et al. |
| 9,844,550 | B2 | 12/2017 | Kang et al. |
| 2005/0059663 | A1 | 3/2005 | Martin et al. |
| 2008/0161280 | A1 | 7/2008 | Gandhi et al. |
| 2015/0225401 | A1 | 8/2015 | Wu et al. |
| 2016/0222003 | A1 | 8/2016 | Kang et al. |

FOREIGN PATENT DOCUMENTS

| | | | | |
|---|---|---|---|---|
| CN | 101925595 | A | | 12/2010 |
| CN | 103130723 | A | | 6/2013 |
| CN | 106146504 | A | * | 11/2016 ........... C07D 471/04 |
| EP | 1633724 | B1 | | 3/2006 |
| EP | 2799435 | A1 | | 11/2014 |
| JP | 2006-519827 | A | | 8/2006 |
| JP | 2009-538896 | A | | 11/2009 |
| JP | 2009-538897 | A | | 11/2009 |
| JP | 2010-514785 | A | | 5/2010 |
| JP | 2016-534143 | A | | 11/2016 |
| KR | 20170037116 | A | * | 4/2017 |
| WO | 02/36576 | A1 | | 5/2002 |
| WO | 03/093261 | A1 | | 11/2003 |
| WO | 2004/080976 | A1 | | 9/2004 |
| WO | 2007/138351 | A2 | | 12/2007 |
| WO | 2007/138355 | A1 | | 12/2007 |
| WO | 2009/063244 | A1 | | 5/2009 |
| WO | 2009/112832 | A1 | | 9/2009 |
| WO | 2012/014221 | A1 | | 2/2012 |
| WO | 2012/019427 | A1 | | 2/2012 |
| WO | 2012/019430 | A1 | | 2/2012 |
| WO | 2012019426 | A1 | | 2/2012 |
| WO | 2012/071684 | A1 | | 6/2012 |
| WO | 2012/072033 | A1 | | 6/2012 |
| WO | 2013078771 | A1 | | 6/2013 |

OTHER PUBLICATIONS

Wuts, Peter. "Protection for the Amino Group" in: Greene's Protective Groups in Organic Synthesis (Michigan, Wiley, 2014), pp. 895-1193. (Year: 2014).*
English Translation of KR-20170037116-A (Song Dong Keun). Published on Apr. 4, 2017. Retrieved from K-PION Korean Patent Information Online Network on Jan. 13, 2022. (Year: 2017).*
Joshua R. Dunetz, Javier Magano, and Gerald A. Weisenburger Organic Process Research & Development 2016 20 (2), 140-177 (Year: 2016).*
Translation of CN106146504. Fan et al. Published Nov. 23, 2016. (Year: 2016).*
Zhu, et al., "Discovery and SAR of orally efficacious tetrahydropyridopyridazinone PARP inhibitors for the treatment of cancer," Bioorganic & Medicinal Chemistry, (2012), vol. 20, No. 15: 4635-4645.
Pinedo et al., "Translational Research: The Role of VEGF in Tumor Angiogenesis," The Oncologist, (2000), vol. 5, (Suppl 1): 1-2.
McMahon "VEGF Receptor Signaling in Tumor Angiogenesis," The Oncologist, (2000), vol. 5, (Suppl. 1): 3-10.
Ye et al., "Design, Synthesis, and Biological Evaluation of a Series of Benzo[de][1,7]naphthyridin-7(8H)-ones Bearing a Functionalized Longer Chain Appendage as Novel PARP1 Inhibitors," J. Med. Chem., 2013, 56:2885-2903.
Lee, et al., "A comparative preclinical study of PARP inhibitors demonstrates superb properties for IDX-1197," AACR Annual Meeting 2018, Apr. 14-18, 2018, Chicago, Illinois, USA.
International Search Report of International Application No. PCT/IB2020/000318 mailed Jan. 18, 2021.
Written Opinion of International Patent Application No. PCT/IB2020/000318 mailed Jan. 18, 2021.

(Continued)

*Primary Examiner* — Amy C Bonaparte
*Assistant Examiner* — Lauren Wells
(74) *Attorney, Agent, or Firm* — McBee Moore & Vanik, IP, LLC

(57) ABSTRACT

The present application provides a method of preparing 4-[3-(3-[(cyclopropylamino)methyl]azetidine-1-carbonyl)-4-fluorobenzyl]phthalazin-1(2H)-one, or a pharmaceutically acceptable salt thereof, intermediates in the preparation thereof, methods of preparing the intermediates, and compositions and products comprising 4-[3-(3-[(cyclopropylamino)methyl]azetidine-1-carbonyl)-4-fluorobenzyl]phthalazin-1(2H)-one made from the methods that result in high purity and yield.

8 Claims, No Drawings

(56) References Cited

OTHER PUBLICATIONS

Lee, et al., "Development of IDX-1197, a novel, selective, and highly potent PARP inhibitor," 28th AACR-NCI-EORTC Molecular Targets and Cancer Therapeutics Conference in Philadelphia, Pennsylvania, USA; Oct. 26-30, 2017.

Tajbakhsh, et al., "Catalyst-Free One-Pot Reductive Alkylation of Primary and Secondary Amines and N,N-Dimethylation of Amino Acids Using Sodium Borohydride in 2,2,2-Trifluoroethanol," Synthesis, (2011), No. 3: 0490-0496.

Benoiton, N. Leo, "Chemistry of Peptide Synthesis", 2006, pp. 50, Taylor & Francis Group LLC.

McKnelly, et al. "Anaphylaxis Induced by Peptide Coupling Agents: Lessons Learned from Repeated Exposure to HATU, HBTU, and HCTU", Journal of Organic Chemistry, 2020, 85, pp. 1764-1768.

Wehrstedt, et al., "Explosive properties of 1-hydroxybenzotriazoles", Journal of Hazerdous Materials, A126 (2005) pp. 1-7.

"List of UN No. 0501 to 0600", Retrieved on Sep. 15, 2022 from "https://en.wikipedia.org/w/index.php?title=List_of_UN_numbers_0501_to_0600&oldid=1077134124", pp. 1-2.

Beyermann, et al., "Effect of tertiary amine on the carbodiimide-mediated peptide synthesis," Int. J. Peptide Protein Res., vol. 37, pp. 252-256 (1991).

Melvin S. Newman and Herbert Boden, Notes-N-Methylpyrrolidone as Solvent for Reaction of Aryl Halides with Cuprous Cyanide, the Journal of Organic Chemistry , 1961 , vol. 26 , pp. 2525-2528.

Mitchell A. Avery, Protective Groups in Organic Synthesis, 1999 , pp. 506-507, 581.

* cited by examiner

PROCESS FOR PREPARING A PHTHALAZINONE DERIVATIVE AND INTERMEDIATES THEREOF

CROSS REFERENCE TO RELATED APPLICATION

This application claims priority to U.S. Ser. No. 63/013,310, filed 21 Apr. 2020, the content of which is incorporated herein by reference in its entirety.

TECHNICAL FIELD

The present invention relates to methods of preparing phthalazinone derivatives which are poly (ADP-ribose) polymerase (PARP) inhibitors, intermediates used in these preparation methods, methods of preparing the intermediates, and compositions and products comprising said derivatives prepared from methods that result in high purity and yield.

BACKGROUND

Patent document 1 (U.S. Pat. No. 9,682,973) discloses phthalazinone derivatives having anti-cancer activity as poly (ADP-ribose) polymerase (PARP) inhibitors, racemates, enantiomers or diastereomers thereof, or pharmaceutically acceptable salts thereof.

The patent document discloses methods of preparing the phthalazinone derivatives, and in particular, in Examples 143 and 171, methods of preparing 4-[3-(3-[(cyclopropylamino)methyl]azetidine-1-carbonyl)-4-fluorobenzyl]phthalazin-1(2H)-one, or a pharmaceutically acceptable salt thereof, as represented in Reaction Scheme 1 below.

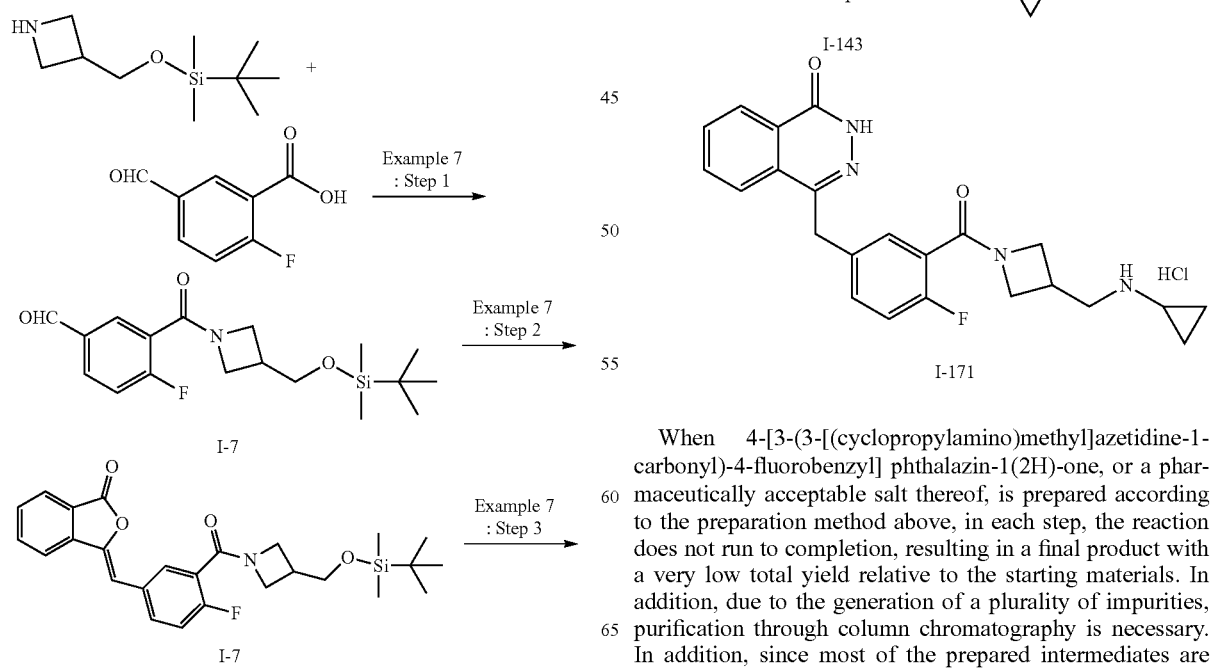

When 4-[3-(3-[(cyclopropylamino)methyl]azetidine-1-carbonyl)-4-fluorobenzyl] phthalazin-1(2H)-one, or a pharmaceutically acceptable salt thereof, is prepared according to the preparation method above, in each step, the reaction does not run to completion, resulting in a final product with a very low total yield relative to the starting materials. In addition, due to the generation of a plurality of impurities, purification through column chromatography is necessary. In addition, since most of the prepared intermediates are present in the liquid phase, it is difficult to achieve a quantitative reaction at each step, and application to mass (e.g., large-scale and commercial) production is difficult due to poor quality reproducibility.

In particular, in the synthesis process of 4-[3-(3-[(cyclopropylamino)methyl]azetidine-1-carbonyl)-4-fluorobenzyl] phthalazin-1(2H)-one (Example 143, Step 2), the reaction is not completed even when the reaction proceeds for 24 hours or longer. Further, due to the generation of a plurality of related materials, an additional purification step, including column chromatography, is necessary to obtain substantially pure sample, which diminishes the final yield.

Technical Problem

An aspect of the present invention is to provide a method of preparing 4-[3-(3-[(cyclopropylamino)methyl]azetidine-1-carbonyl)-4-fluorobenzyl]phthalazin-1 (2H)-one, or a pharmaceutically acceptable salt thereof, where one or more intermediates are obtained in a solid phase, and where the reduction in the formation of impurities avoids the need for an additional purification step, thereby increasing the total yield in a manner that is suitable for mass (e.g., large-scale and commercial) production.

Another aspect is to provide one or more novel intermediates which can be used in the above-described preparation method.

Another aspect is to provide a method of preparing the one or more intermediates.

Compositions and products containing the compound of Formula 1, or a pharmaceutically acceptable salt thereof, prepared from the methods of the present invention are also provided.

Other objectives and advantages of the present invention will become apparent from the following detailed descriptions along with the appended drawings. The contents not described in the present specification may be sufficiently recognized and inferred by those skilled in the art or similar fields of the present invention, and thus description thereof is omitted.

Technical Solution

According to an aspect of the present invention, there is provided a method of preparing a compound of Formula 1, or a pharmaceutically acceptable salt thereof:

[Formula 1]

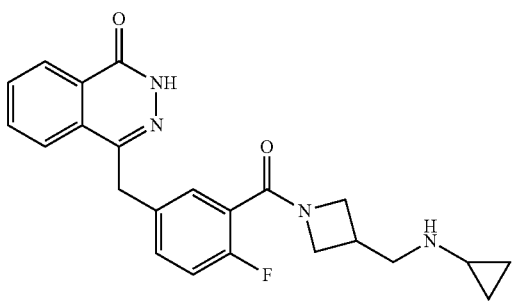

the method comprising a step (a2) of deprotecting a compound of Formula 4 to prepare the compound of Formula 1:

[Formula 4]

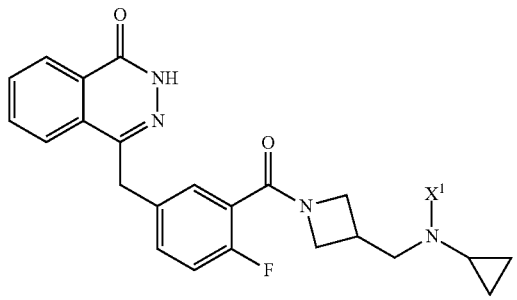

wherein $X^1$ is an amine protecting group.

According to another aspect of the present invention, there is provided a method of preparing a compound of Formula 4, comprising a step (a1) of reacting a compound of Formula 2 with a compound of Formula 3:

[Formula 2]

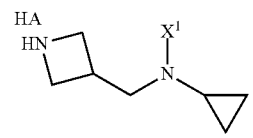

wherein, $X^1$ is an amine protecting group, and HA is an acid which forms an acid addition salt; and

[Formula 3]

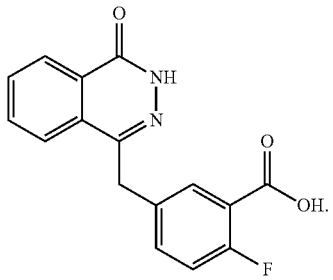

According to another aspect of the present invention, there is provided a method of preparing a compound of Formula 2,

[Formula 2]

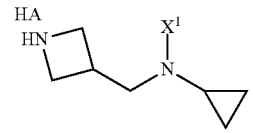

the method comprising:
a step (b1) of introducing an amine protecting group $X^1$ into a compound of Formula 6 to prepare a compound of Formula 7; and
a step (b2) of removing an azetidine nitrogen protecting group $X^2$ from the compound of Formula 7 to prepare the compound of Formula 2:

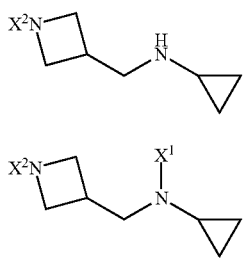

[Formula 6]

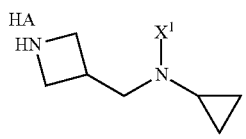

[Formula 7]

wherein, $X^1$ is an amine protecting group,
$X^2$ is an azetidine nitrogen protecting group, and
HA is an acid which forms an acid addition salt.

According to another aspect of the present invention, there is provided a compound of Formula 2:

[Formula 2]

(structure shown)

wherein, $X^1$ is an amine protecting group,
HA is an acid which forms an acid addition salt.

According to another aspect of the present invention, there is provided a compound of Formula 4:

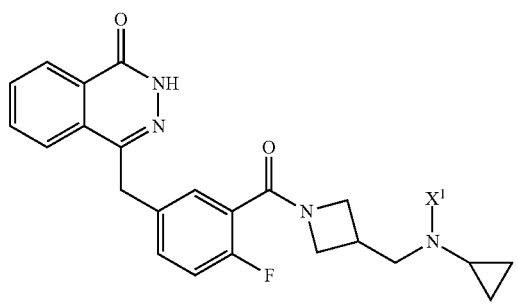

[Formula 4]

wherein $X^1$ is an amine protecting group.

According to another aspect of the present invention, there is provided a compound of Formula 7:

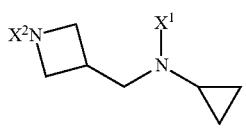

[Formula 7]

wherein, $X^1$ is an amine protecting group, and $X^2$ is an azetidine nitrogen protecting group.

Effect of the Invention

According to an aspect of the present invention, one or more intermediates generated according to the present method may be obtained in a solid phase, thus resulting in more convenient separation of the intermediates. In each process, the reaction to generate intermediates may be completed with minimal side reactions, and low levels of impurities, and thus there is no need to perform column chromatography, which was previously needed for separation and purification to obtain substantially pure compound. Due to the reduction in the generation of impurities and easy separation of the intermediates, a final product may be obtained with high purity and high yield. Therefore, the preparation method according to an aspect of the present invention may prepare 4-[3-(3-[(cyclopropylamino)methyl]azetidine-1-carbonyl)-4-fluorobenzyl]phthalazin-1 (2H)-one, or a pharmaceutically acceptable salt thereof, with higher purity and higher yield, and more economically, and thus is suitable for mass (e.g., large-scale and commercial) production.

DETAILED DESCRIPTION OF THE INVENTION

Hereinafter, the present invention will be described in greater detail.

Unless otherwise defined, all technical terms used in the present invention have the same meanings as commonly understood by those skilled in the related art of the present invention. In addition, although a preferred method or example is described in the specification, those similar or equivalent thereto fall within the scope of the present invention. In addition, the term "comprising" is intended to have an inclusive meaning and permits the inclusion of additional elements other than the listed elements.

Unless otherwise indicated, all numbers expressing quantities of ingredients, properties such as molecular weight, reaction conditions, and so forth as used in the specification and claims are to be understood as being modified in all instances by the term "about."

As used herein, the term "compound of Formula" is not intended to be limited to the Formula. When one structure is illustrated, unless stated otherwise, it is understood that all possible stereoisomers and tautomers thereof are included.

The term "protecting group" refers to a functional group which protects, from unintentional reaction, a functional group such as an amino group or alcohol group, by being bonded thereto via a covalent bond, and allows the functional group to be regenerated (i.e., de-protected) after treatment of the protecting group with a suitable reagent.

As used herein, the term "intermediates generated according to the present method are obtained in a solid phase" means that the intermediates are obtained in a solid form by, for example, filtration and drying, or similar steps known in the art.

The term "ambient temperature" refers to an indoor ambient temperature in the range of about 1° C. to about 30° C.

The contents of all publications cited as reference documents herein are incorporated in the present specification by reference in their entirety.

Explanations and embodiments disclosed in the present invention may be applied to other explanations and embodiments, respectively. That is, all combinations of various elements disclosed in the present invention belong to the scope of the present invention. Additionally, the scope of the present invention should not be limited by the specific descriptions described herein below.

An aspect of the present invention provides a method of preparing a compound of Formula 1, or a pharmaceutically acceptable salt thereof,

[Formula 1]

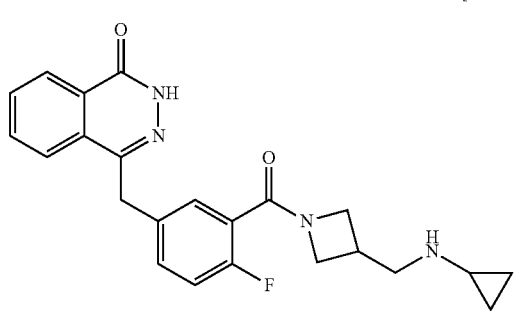

the method including
a step (a2) of deprotecting a compound of Formula 4 to prepare the compound of Formula 1:

[Formula 4]

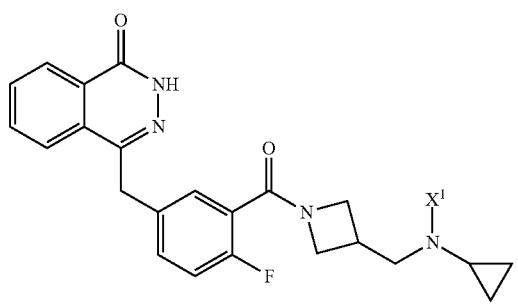

wherein $X^1$ is an amine protecting group.

The compound of Formula 4 may be prepared by a step (a1) of reacting a compound of Formula 2 with a compound of Formula 3:

[Formula 2]

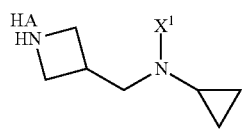

wherein $X^1$ is an amine protecting group, and HA is an acid which forms an acid addition salt;

[Formula 3]

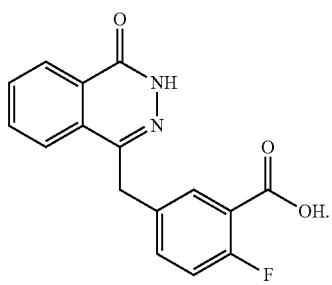

Another aspect of the present invention provides a method of preparing a compound of Formula 4, including a step (a1) of reacting a compound of Formula 2 with a compound of Formula 3:

[Formula 2]

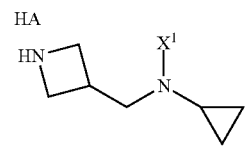

[Formula 3]

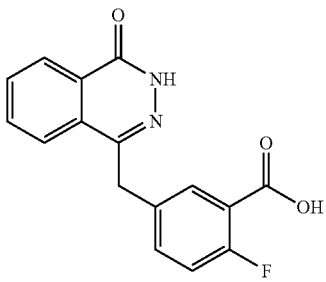

wherein
$X^1$ is an amine protecting group, and
HA is an acid which forms an acid addition salt.

HA, as shown above, may be any acid which forms an acid addition salt. For example, the acid addition salt may be a hydrohalogenic acid salt. The hydrohalogenic acid may include hydrochloric acid (HCl), hydrobromic acid (HBr), or hydroiodic acid (HI), and preferably, hydrochloric acid (HCl).

In the step (a1), the compound of Formula 4 may be obtained by amide bond between the compound of Formula 2 and the compound of Formula 3. In the step (a2), the compound of Formula 1 may be obtained by removing $X^1$ which is a protecting group for the amine group of the compound of Formula 4.

In one embodiment, the method of preparing the compound of Formula 1, or a pharmaceutically acceptable salt thereof, may be represented by Reaction Scheme 2 below.

[Reaction Scheme 2]

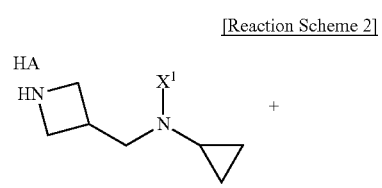

Formula 2

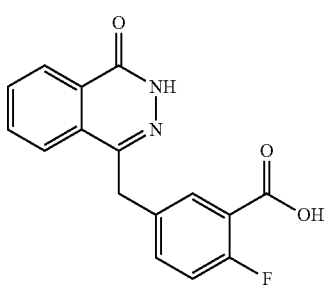

Formula 3

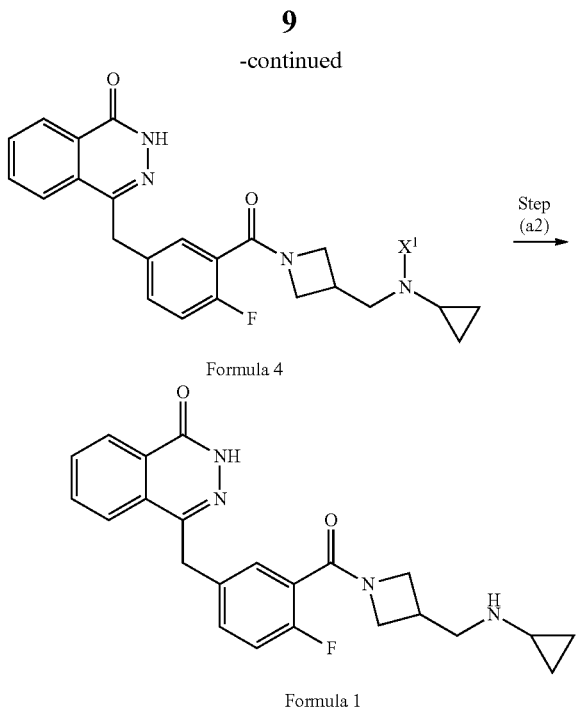

Formula 4

Formula 1

The compound of Formula 3 used in the step (a1) may be prepared according to any method known in the art, for example, a method disclosed in WO 2004/080976 (see section b in "Synthesis of Key Intermediates").

In one embodiment, the compound of Formula 2 may be in the form of hydrochloride salt wherein HA is hydrochloric acid. $X^1$ may be any amine protecting group capable of protecting the amine group to which $X^1$ is bonded in the reaction of step (a1). This amine protecting group may include, but is not limited to, fluorenylmethoxycarbonyl (Fmoc), trifluoroacetyl (Tfa), or p-methoxybenzyl (PMB).

The step (a1) of preparing the compound of Formula 4 may be carried out under any condition which allows formation of amide bond between the azetidine amine of the compound of Formula 2 and the carboxyl group of the compound of Formula 3.

In one embodiment, the step (a1) may be carried out in the presence of an amide coupling reagent. The amide coupling reagent refers to a reagent which activates a carboxyl group of a reactant to be able to form an amide group during reaction with an amine. The amide coupling reagent may include, but not limited to, trimethylacetyl chloride, 1,1′-carbonyldiimidazole, N-(3-dimethylaminopropyl)-N′-ethyl-carbodiimide hydrochloride(EDC), or any combination thereof.

The step (a1) may be carried out in the presence of a base, for example, in the presence of at least one base selected from the group consisting of diisopropylethylamine, triethylamine, N-methylmorpholine, and any combination thereof.

In one embodiment, the step (a1) may be carried out in the presence of both at least one amide coupling reagent and at least one base.

In one embodiment, the step (a1) may be carried out in the presence of both at least one amide coupling agent selected from the group consisting of trimethylacetyl chloride, 1,1′-carbonyldiimidazole, N-(3-dimethylaminopropyl)-N′-ethyl-carbodiimide hydrochloride(EDC), and any combination thereof, and at least one base selected from the group consisting of diisopropylethylamine, triethylamine, N-methylmorpholine, and any combination thereof.

For the reaction in the step (a1), a solvent which does not inhibit the reaction may be used. For example, the solvent may be selected from acetonitrile, acetone, toluene, tetrahydrofuran, dichloromethane, chloroform, N,N-dimethylformamide, and any combination thereof. In one embodiment, the solvent may be toluene.

The reaction in the step (a1) may be carried out at a temperature of about −20° C. to a reflux temperature, and in some embodiments, at about −20° C. to about 120° C., and in other embodiments, about −10° C. to about 40° C.

In the step (a1), the compound of Formula 4, which is the product of the reaction, may be obtained in solid phase. Thus, the compound of Formula 4 may be obtained in solid form by filtration and drying.

The step (a2) of preparing the compound of Formula 1 is a reaction of removing the amine protecting group $X^1$ from the compound of Formula 4, and the reaction conditions for removing the amine protecting group $X^1$ may vary depending on the type of the amine protecting group $X^1$.

In one embodiment, the step (a2) of preparing the compound of Formula 1 may include, when $X^1$ is fluorenylmethoxycarbonyl (Fmoc), reacting the compound of Formula 4 with a non-nucleophilic base. The non-nucleophilic base is not limited to specific types, and may be any non-nucleophilic base which can effectively remove the amine protecting group $X^1$. For example, the non-nucleophilic base may be selected from piperidine, diisopropylethylamine, 1,8-diazabicyclo[5,4,0]undec-7-ene, and any combination thereof. In this case, a solvent for the reaction in the step (a2) may be acetonitrile, tetrahydrofuran, N,N-dimethylformamide, or any combination thereof. For example, when $X^1$ is fluorenylmethoxycarbonyl (Fmoc), the non-nucleophilic base and the solvent may be, respectively, piperidine and acetonitrile, diisopropylethylamine and tetrahydrofuran, or 8-diazabicyclo[5,4,0]undec-7-ene and N,N-dimethylformamide.

In another embodiment, in the step (a2), when $X^1$ is trifluoroacetyl (Tfa), the compound of Formula 4 may be reacted with an alkali base. The alkali base is not limited to specific types, and may be any alkali base which can effectively separate the amine protecting group $X^1$. For example, the alkali base may be potassium hydroxide, potassium carbonate, sodium hydroxide, sodium carbonate, or any combination thereof. In this case, a solvent for the reaction in the step (a2) may be a solvent in which water is added to a $C_1$-$C_4$ linear alcohol, a $C_1$-$C_4$ branched alcohol, or any combination thereof. For example, when $X^1$ is trifluoroacetyl (Tfa), the alkali base and the solvent may be, respectively, potassium hydroxide and isopropyl alcohol/water, potassium carbonate and methanol/water, sodium hydroxide and methanol/water, or sodium carbonate and ethanol/water.

In still another embodiment, in the step (a2), when $X^1$ is p-methoxybenzyl (PMB), the compound of Formula 4 may be reacted with an acid. The acid is not limited to specific types, and may be any acid which can effectively remove the amine protecting group. For example, trifluoroacetic acid may be used as the reagent and a solvent. In this case, in the reaction of the step (2), a ratio (w/v) of the weight of the compound of Formula 4 and the volume of trifluoroacetic acid may be about 1:5 to about 1:40. For example, when $X^1$ is p-methoxybenzyl (PMB), a ratio (w/v) of the compound of Formula 4 to trifluoroacetic acid, which are used in the reaction of the step (a2), may be about 1:10.

In the step (a2), the compound of Formula 1, which is the product of the reaction, may be obtained in solid phase. Thus, the compound of Formula 1 may be obtained in solid form by filtration and drying.

A step (a3) of preparing an acid addition salt of the compound of Formula 1 by reacting the compound of Formula 1 with an acid may be further performed to thereby prepare a pharmaceutically acceptable salt of the compound of Formula 1. The preparing of an acid addition salt of the compound of Formula 1 may be performed using a suitable method by those skilled in the art based on the common knowledge in the field of organic chemistry. The acid addition salt of the compound of Formula 1 may be any pharmaceutically acceptable acid addition salt, for example, an acid addition salt formed from a free acid. The free acid may be an inorganic acid or an organic acid. The inorganic acid may be hydrochloric acid, hydrobromic acid, sulfuric acid, or phosphoric acid. The organic acid may be, but not limited to, acetic acid, trifluoroacetic acid, oxalic acid, maleic acid, succinic acid, fumaric acid, adipic acid, L- or D-tartaric acid, DL-tartaric acid, citric acid, lactic acid, benzoic acid, mandelic acid, salicylic acid, cinnamic acid, methane sulfonic acid, ethane sulfonic acid, p-toluene sulfonic acid, glycolic acid, pyruvic acid, glucuronic acid, glutamic acid, aspartic acid, or any combination thereof.

In one embodiment, the acid addition salt may be an inorganic acid addition salt, and in an embodiment, a hydrochloric acid addition salt. The reaction in the step (a) of preparing an acid addition salt of the compound of Formula 1 may be carried out in any solvent which does not inhibit formation of the acid addition salt. For example, the solvent may be selected from alcohol, ketone, ether, acetic acid esters, dichloromethane, chloroform, and any combination thereof, and in some embodiments, may be a $C_1$-$C_5$ alcohol, a $C_3$-$C_{10}$ ketone, a $C_2$-$C_{10}$ ether, $C_2$-$C_4$ alkyl acetate, dichloromethane, chloroform, or any combination thereof.

The reaction in the step (a3) may be carried out at a temperature of about −20° C. to a reflux temperature, and in some embodiments, at a temperature ranging from about −20° C. to about 50° C., and in other embodiments, at a temperature ranging from about −10° C. to about 30° C.

In one embodiment, a hydrochloride of the compound of Formula 1 may be prepared by adding, at a temperature ranging from about −20° C. to a reflux temperature, anhydrous hydrochloric acid or concentrated hydrochloric acid to the compound represented by Formula 1, with a solvent of an alcohol, a mixture of alcohol and ketone, a mixture of alcohol and dichloromethane, a mixture of alcohol and chloroform, a mixture of alcohol and ether, or a mixture of alcohol and acetic acid esters. For example, the alcohol, the ketone, the ether, and the acetic acid esters may be, respectively, a $C_1$-$C_5$ alcohol, a $C_3$-$C_{10}$ ketone, a $C_2$-$C_{10}$ ether, and $C_2$-$C_4$ alkyl acetate.

In one embodiment, a hydrochloride of the compound of Formula 1 may be prepared by adding, at a temperature ranging from about −20° C. to a reflux temperature or less, anhydrous hydrochloric acid or concentrated hydrochloric acid to the compound represented by Formula 1, with a solvent of an alcohol, a mixture of alcohol and ketone, a mixture of alcohol and dichloromethane, a mixture of alcohol and chloroform, or a mixture of alcohol and ether, and then filtering and drying the thus-formed solid. For example, the alcohol, the ketone, and the ether may be, respectively, a $C_1$-$C_5$ alcohol, a $C_3$-$C_{10}$ ketone, and a $C_2$-$C_{10}$ ether.

In the step (a3), the acid addition salt of the compound of Formula 1, which is the product of the reaction, may be obtained in solid phase. Thus, the acid addition salt of the compound of Formula 1 may be obtained in solid form by filtration and drying.

In another aspect, there is provided a method of preparing a compound of Formula 2 as represented above,
the method including:
the step (b1) of preparing a compound of Formula 7 by introducing an amine protecting group $X^1$ into a compound of Formula 6; and
the step (b2) of preparing the compound of Formula 2 by removing an azetidine nitrogen protecting group $X^2$ from the compound of Formula 7:

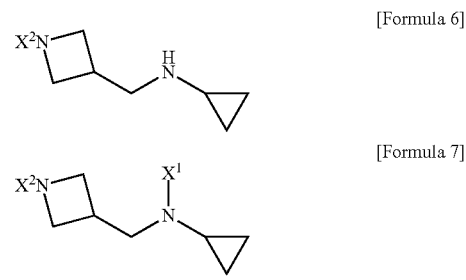

[Formula 6]

[Formula 7]

wherein, in the above Formula, $X^1$ is an amine protecting group, and $X^2$ is an azetidine nitrogen protecting group.

In one embodiment, the compound of Formula 2 may be an acid addition salt, wherein HA in Formula 2 is hydrochloric acid.

In the reaction of the step (b1) of preparing the compound of Formula 7 by introducing an amine protecting group $X^1$ into the compound of Formula 6, the amine protecting group $X^1$ may protect a secondary amine group which does not belong to the nitrogen of the azetidine ring of the compound of Formula 7, when the compound of Formula 2 is prepared from the compound of Formula 7, i.e., in the reaction of the step (b2). Accordingly, the amine protecting group $X^1$ may be any protecting group capable of protecting a secondary amine group which is not included in the azetidine ring, in the preparation of the acid addition salt compound of Formula 2 by deprotection reaction of the azetidine nitrogen protecting group $X^2$ of the compound of Formula 7. For example, the amine protecting group $X^1$ may be fluorenylmethoxycarbonyl (Fmoc), trifluoroacetyl (Tfa), or p-methoxybenzyl (PMB).

In the reaction of the step (b1), a reagent capable of introducing the amine protecting group $X^1$ to the compound of Formula 6 may vary depending on a specific type of the amine protecting group $X^1$. For example, the reaction of the step (b1) may be carried out by reacting the compound of Formula 6 with a reagent selected from fluorenylmethoxycarbonyl chloride, trifluoroacetic acid anhydride, 4-methoxybenzyl chloride, and any combination thereof.

The reaction of the step (b1) may be carried out in the presence of a base. The base may be any base as long as it does not inhibit the reaction of introducing the amine protecting group $X^1$ into the compound of Formula 6. For example, the base may be a tertiary amine. For example, the tertiary amine may be selected from diisopropylethylamine, triethylamine, N-methylmorpholine, and any combination thereof.

In one embodiment, the reaction of the step (b) may be carried out in the presence of both a reagent capable of introducing the amine protecting group $X^1$, and a base. For example, the reaction of the step (b) may be carried out in the presence of both a reagent selected from fluorenylmethoxycarbonyl chloride, trifluoroacetic acid anhydride, 4-methoxybenzyl chloride, and any combination thereof, and a base selected from diisopropylethylamine, triethylamine, N-methylmorpholine, and any combination thereof.

A solvent used in the reaction of the step (b) is not limited to specific types as long as it does not inhibit the reaction. For example, the solvent may be selected from acetonitrile, toluene, tetrahydrofuran, dichloromethane, chloroform, N,N-dimethylformamide, and any combination thereof.

The reaction of the step (b1) may be carried out at a temperature of about −20° C. to a reflux temperature or less, and in some embodiments, at a temperature ranging from about −20° C. to about 120° C., and in other embodiments, at a temperature ranging from about −10° C. to about 80° C.

The reaction of the step (b2) of preparing the compound of Formula 2, which is carried out after the reaction of the step (b1), may include the process of removing the azetidine nitrogen protecting group $X^2$ from the compound of Formula 7 and substituting the same with hydrogen instead. The azetidine nitrogen protecting group $X^2$ may be any protecting group which can be removed, leaving the amine protecting group $X^1$ not removed, and substituted with hydrogen. For example, the azetidine nitrogen protecting group $X^2$ may be selected from the group consisting of butoxycarbonyl (Boc), triphenylmethyl (Trt), and tetrahydropyranyl (THP). In one embodiment, the azetidine nitrogen protecting group $X^2$ is butoxycarbonyl (Boc).

The process of substitution with hydrogen in the step (b2) may be carried out at a temperature of about −20° C. to a reflux temperature, and in some embodiments, at a temperature ranging from about 0° C. to about 90° C.

For example, the process of substitution with hydrogen in the reaction of the step (b2) may be carried out by reacting the compound of Formula 7 with an acid, thus removing the azetidine nitrogen protecting group $X^2$ from the compound of Formula 7, and substituting the same with hydrogen. The acid is not limited to specific types, and may be any acid capable of effectively removing the azetidine nitrogen protecting group $X^2$, and forming the acid addition salt of Formula 2. For example, the acid may be hydrohalogenic acid, for example, hydrochloric acid, hydrobromic acid, or hydroiodic acid. In one embodiment, the acid may be an anhydrous hydrochloric acid or concentrated hydrochloric acid.

A solvent used in the process of substitution with hydrogen in the reaction of the step (b2) may be any solvent which does not inhibit the corresponding reaction. For example, when the azetidine nitrogen protecting group $X^2$ is butoxycarbonyl (Boc), the solvent may be selected from acetone, ethyl acetate, a $C_1$-$C_4$ linear or branched alcohol, and any combination thereof.

In one embodiment, when $X^2$ is butoxycarbonyl (Boc), the acid and the solvent used in the reaction of the step (b2) may be, respectively, hydrochloric acid and acetone, or hydrochloric acid and ethyl acetate, or hydrochloric acid and isopropyl alcohol, or hydrochloric acid and ethanol, or hydrochloric acid and methanol.

The acid addition salt of Formula 2 may be prepared by evaporation without a post-treatment process or by precipitation with addition of a suitable solvent, after the removal of $X^2$ from the compound of Formula 7 with addition of an acid into the solvent in the reaction of the step (b2) and the substitution with hydrogen instead. The suitable solvent added to precipitate the acid addition salt may be selected from ethylacetate, acetone, n-hexane, isopropyl alcohol, and any combination thereof, but is not limited thereto. Any suitable solvent may be selected by one of ordinary skill in the art in consideration of the required conditions for the solvent in the corresponding reaction.

In one embodiment, a hydrochloride salt among the acid addition salts of the compound of Formula 2, may be prepared by adding concentrated hydrochloric acid to the compound of Formula 7 in methanol and allowing a reaction to take place, concentrating the reaction product under reduced pressure, and then refluxing with addition of ethyl acetate, stirring at ambient temperature, and then filtering and drying.

The compound of Formula 6 may be prepared by the step (b0) of reductive amination reaction of a compound represented by Formula 5:

[Formula 5]

wherein, in Formula 5, $X^2$ is an azetidine nitrogen protecting group.

In the reaction of the step (b0), the reductive amination reaction of the compound of Formula 5 may be carried out by one of ordinary skill in the art based on the common knowledge known in the art. In one embodiment, in the reaction of the step (b0), by proceeding with the reductive amination using trifluoroethanol as a solvent and sodium borohydride without a catalyst or an additive, the compound of Formula 6 may be prepared with a high yield (see Synthesis 2011, No. 3, p. 490-496).

In one embodiment, the method of preparing the compound of Formula 1, or a pharmaceutically acceptable salt thereof, may be represented by Reaction Scheme 3 below.

[Reaction Scheme 3]

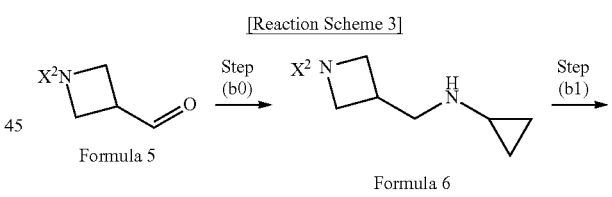

Formula 5

Formula 6

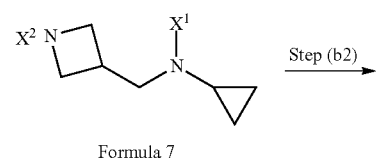

Formula 7

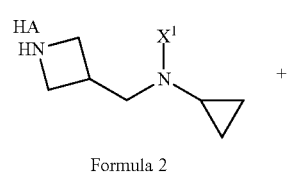

Formula 2

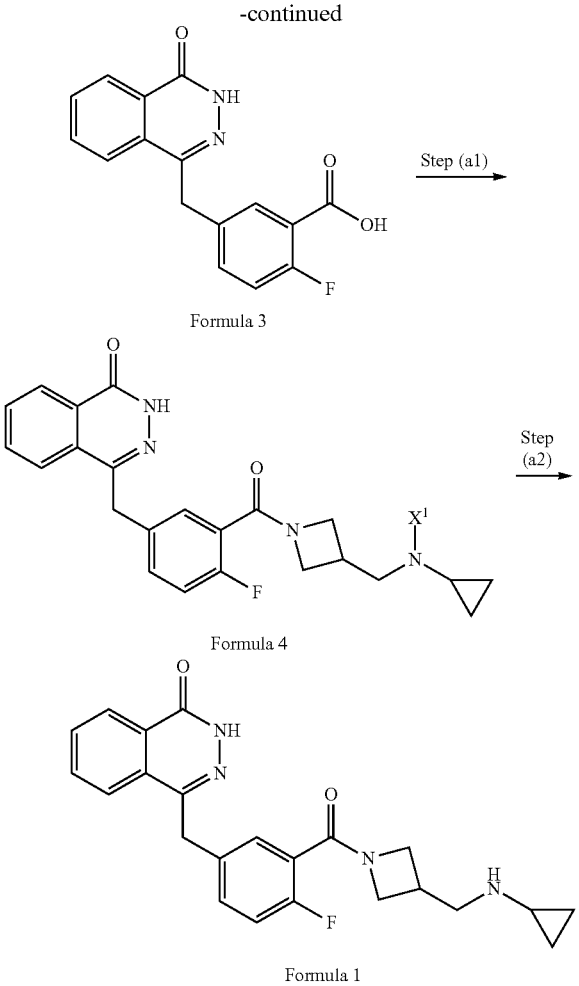

Formula 3

Formula 4

Formula 1

According to an exemplary preparation method of the present invention, e.g., represented in Reaction Scheme 3, 4-[3-(3-[(cyclopropylamino)methyl]azetidine-1-carbonyl)-4-fluorobenzyl]phthalazin-1(2H)-one, or a pharmaceutically acceptable salt thereof, can be prepared with higher purity and higher yield. In one embodiment, the yield may be about 3 to 10 times, preferably, 5 to 8 times higher than that obtained in a known method, e.g., disclosed in U.S. Pat. No. 9,682,973. In another embodiment, the final product obtained in the present method may have at least 90%, preferably, at least 95%, more preferably, at least 97%, most preferably, at least 99% of purity (including 99.5% or 99.9%) when identified by the percent area of HPLC.

In the method of preparing the compound of Formula 1, or a pharmaceutically acceptable salt thereof, according to an aspect of the present invention, one or more intermediates generated according to the present method (for example, a compound of Formula 2 or 4) may be obtained in a solid phase, thus resulting in more convenient separation of the intermediates. In each process, the reaction to generate intermediates is completed and the generation of related materials is low, and thus there is no need to perform column chromatography, which was previously needed for separation and purification. Due to the reduction in the generation of related materials and easy separation of the intermediates, a final product may be obtained with high yield. In addition, since column chromatography, which is a process not suitable for mass (e.g., large-scale and commercial) production, may be avoided, and quality reproducibility may be improved, and thus the method may be advantageously applied to mass production.

In another aspect, there is provided a compound of Formula 2:

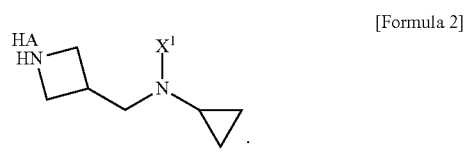

[Formula 2]

wherein, in Formula 2, $X^1$ is an amine protecting group, and HA is an acid which forms an acid addition salt.

The amine protecting group $X^1$ may be selected from the group consisting of fluorenylmethoxycarbonyl (Fmoc), trifluoroacetyl (Tfa), and p-methoxybenzyl (PMB), but is not limited thereto.

HA may be any acid which forms an acid addition salt. For example, HA may be a hydrohalogenic acid. The hydrohalogenic acid may be hydrochloric acid, hydrobromic acid, or hydroiodic acid, and, for example, may be hydrochloric acid.

The compound of Formula 2 is a novel intermediate compound in solid phase, which was not used in existing methods for the preparation of the compound of Formula 1, or a pharmaceutical acceptable salt thereof, as described above. When the compound of Formula 2 is used as an intermediate, all the products of the subsequent steps, including the intermediate, can be obtained in a solid phase. Purification steps may then be minimized, which results in a method for preparing the compound of Formula 1, or a pharmaceutically acceptable salt thereof, with high yield and high purity. Therefore, the compound of Formula 1, or a pharmaceutically acceptable salt, thereof may be mass (e.g., large-scale and commercial) produced with high yield and high purity.

In one embodiment, the compound of Formula 2 may be selected from the group consisting of the following compounds:

(9H-fluorene-9-yl)methyl(azetidin-3-ylmethyl)(cyclopropyl)carbamate hydrochloride of Formula 2a

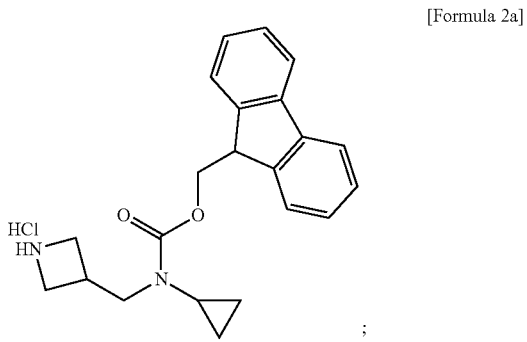 [SMILES: Cl ; O=C(OCC1c2ccccc2-c2ccccc21)N(CC1CNC1)C1CC1]

[Formula 2a]

;

N-(azetidin-3-ylmethyl)-N'-cyclopropyl-2,2,2-trifluoroacetamide hydrochloride of Formula 2b

[Formula 2b]

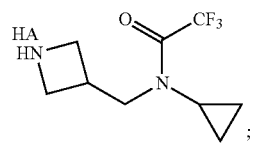

and

N-(azetidin-3-ylmethyl)-N'-(4-methoxybenzyl)cyclopropanamine hydrochloride of Formula 2c

[Formula 2c]

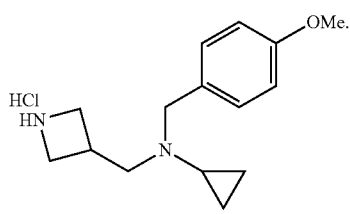

In another aspect, there is provided a compound of Formula 4:

[Formula 4]

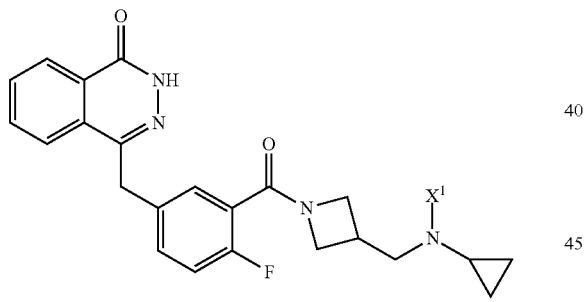

wherein $X^1$ is an amine protecting group.

The amine protecting group $X^1$ may be selected from the group consisting of fluorenylmethoxycarbonyl (Fmoc), trifluoroacetyl (Tfa), and p-methoxybenzyl (PMB), but is not limited thereto.

The compound of Formula 4 is a novel intermediate compound in solid phase, which was not used in existing methods for the preparation of the compound of Formula 1, or a pharmaceutical acceptable salt thereof, as described above. When the compound of Formula 4 is used as an intermediate, the compound of Formula 1 may be obtained in a solid phase. Purification steps may then be minimized, which results in a method of preparing the compound of Formula 1, or a pharmaceutically acceptable salt thereof, with high yield and high purity. Therefore, the compound of Formula 1, or a pharmaceutically acceptable salt thereof, may be produced on mass (e.g., large-scale and commercial) produced with high yield and high purity.

In one embodiment, the compound of Formula 4 may be selected from the group consisting of the following compounds:

(9H-fluorene-9-yl)methyl cyclopropyl([1-(2-fluoro-5-[(4-oxo-3,4-dihydrophthalazin-1-yl)methyl]benzoyl)azetidin-3-yl]methyl)carbamate of Formula 4a

[Formula 4a]

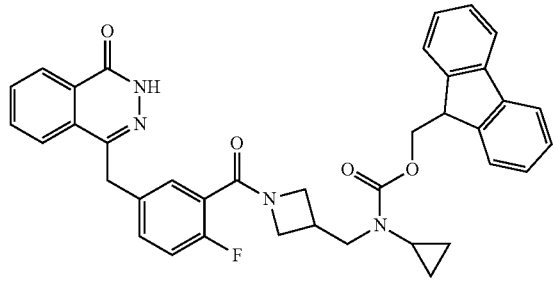

N-cyclopropyl-2,2,2-trifluoro-N'-([1-(2-fluoro-5-[(4-oxo-3,4-dihydrophthalazin-1-yl)methyl]benzoyl)azetidin-3-yl]methyl))acetamide of Formula 4b

[Formula 4b]

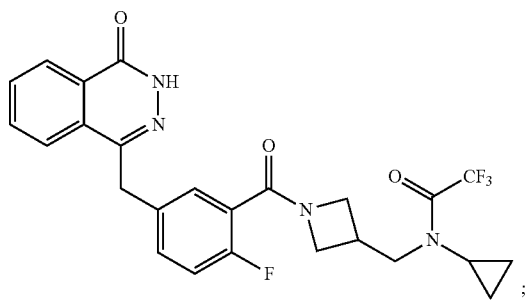

4-(3-[3-([cyclopropyl(4-methoxybenzyl)amino]methyl)azetidin-1-carbonyl]-4-fluorobenzyl)phthalazin-1(2H)-one of Formula 4c

[Formula 4c]

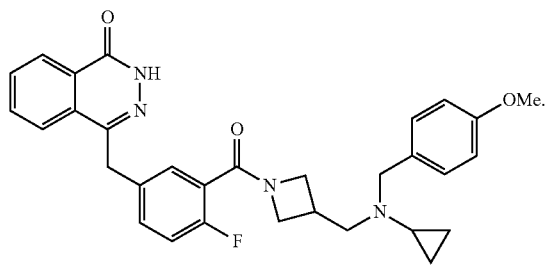

In another aspect, there is provided a compound of Formula 7:

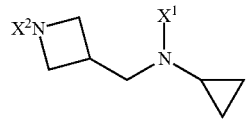

[Formula 7]

wherein $X^1$ is an amine protecting group, and
$X^2$ is an azetidine nitrogen protecting group.

The amine protecting group $X^1$ may be selected from the group consisting of fluorenylmethoxycarbonyl (Fmoc), trifluoroacetyl (Tfa), and p-methoxybenzyl (PMB), but is not limited thereto.

The azetidine nitrogen protecting group $X^2$ may be selected from the group consisting of butoxycarbonyl (Boc), triphenylmethyl (Trt), and tetrahydropyranyl (THP). In one embodiment, the azetidine nitrogen protecting group $X^2$ may be butoxycarbonyl (Boc).

The compound of Formula 7 is a novel intermediate compound, which was not used in existing methods for the preparation of the compound of Formula 1, or a pharmaceutical acceptable salt thereof, as described above.

In one embodiment, the compound of Formula 7 may be selected from the group consisting of the following compounds:

tert-butyl 3-([[[(9H-fluorene-9-yl)methoxy]carbonyl)(cyclopropyl) amino]methyl)azetidin-1-carboxylate of Formula 7a

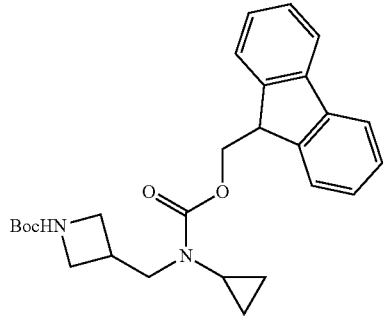

[Formula 7a]

tert-butyl 3-[(cyclopropyl-2,2,2-trifluoroacetamido) methyl] azetidin-1-carboxylate of Formula 7b

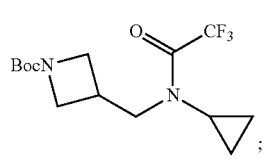

[Formula 7b]

and tert-butyl 3-([cyclopropyl(4-methoxybenzyl)amino] methyl)azetidin-1-carboxylate of Formula 7c

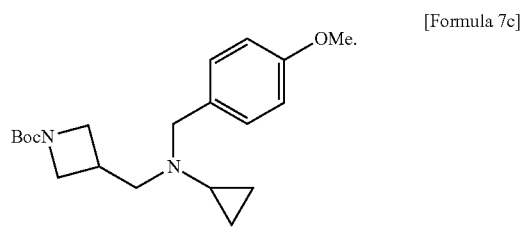 [SMILES: COc1ccc(CN(CC2CN(C(=O)OC(C)(C)C)C2)C2CC2)cc1]

[Formula 7c]

In another aspect of the invention, the methods of the present invention are used to prepare a drug substance, pharmaceutical composition, or medicament comprising the compound of Formula 1, or a pharmaceutically acceptable salt thereof. When the compound of Formula 1, or a pharmaceutically acceptable salt thereof, is used as a drug substance, the intermediate compounds described herein may be present as an impurity. The amount of each of the compounds of Formulas 2 to 7, when present as an impurity, may be controlled to be present at trace levels, for example, to be not more than about 1.0% or less, about 0.5% or less, about 0.2% or less, about 0.1% or less, of the drug substance, or to be not present at all.

Thus, in one aspect, substantially pure forms of the compound of Formula 1 prepared by the methods of the present invention are provided for use as a drug substance in the preparation of a pharmaceutical composition or medicament. In one embodiment, the present invention encompasses pharmaceutical compositions comprising substantially pure drug substance, wherein the compound of Formula 1, or a pharmaceutically acceptable salt thereof, is present in the drug substance in an amount greater than about 90%, about 95%, about 97%, about 99%, about 99.5%, or about 99.9%. Percent purity may be determined using well-known methods in the art. For example, percent purity may be determined by reference to the percentage of measured peak area from the sum of peak area of all peaks under suitable chromatography (e.g., HPLC) detection conditions.

In one aspect, the present invention therefore provides pharmaceutical compositions comprising an effective amount of a compound of Formula 1, or a pharmaceutically acceptable salt thereof, as an active ingredient, wherein said compound is prepared from the methods of the present invention (e.g., one or more of the intermediates described herein and Reaction Scheme 1 and Reaction Scheme 2). The pharmaceutical compositions of the invention may be administered in patients to treat cancers, including cancers sensitive to PARP inhibitors. Such formulations may include binders, fillers, disintegrants, lubricants, coloring agents and preservatives, and other pharmaceutically acceptable excipients.

In another non-limiting embodiment, the present invention provides a product comprising a compound of Formula 1,

[Formula 1]

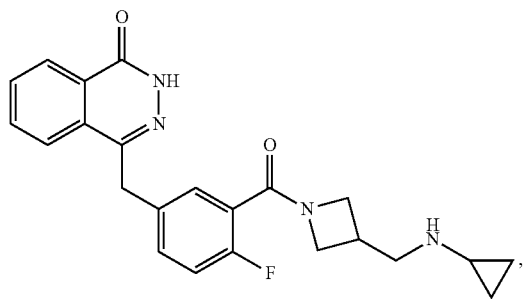

or a pharmaceutically acceptable salt thereof, wherein the compound of Formula 1, or the pharmaceutically acceptable salt thereof, is produced by the methods of the present invention described above, as for example, illustrated in Reaction Scheme 2 and Reaction Scheme 3.

Hereinafter, the present invention will be described in more detail with reference to the following examples. However, these examples are for illustrative purposes only, and the invention is not intended to be limited by these Examples.

Example 1

Preparation of tert-butyl 3-[(cyclopropylamino)methyl]azetidin-1-carboxylate (Formula 6a)

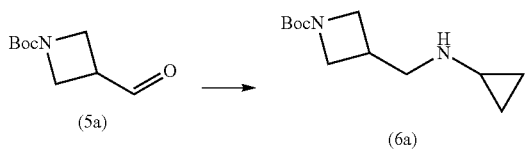

1.0 kg of tert-butyl 3-formylazetidin-1-carboxylate was added into a reactor, and 6.5 kg of trifluoroethanol was added thereto. 0.3 kg of cyclopropylamine was added at 0° C., stirring at ambient temperature for 1 hour, followed by cooling the reactor down to 0° C. 0.2 kg of sodium borohydride was slowly added and stirred at ambient temperature for 1 hour, and then the reactor was cooled down to 0° C. After 10.0 kg of water was slowly added thereto, the reaction mixture was extracted with 6.7 kg of dichloromethane, and the thus-obtained aqueous layer was further extracted with 6.7 kg of dichloromethane. The organic layer was washed with a 15% sodium chloride aqueous solution, treated with 0.5 kg of anhydrous magnesium sulfate, filtered and then concentrated under reduced pressure, to thereby yield 0.98 kg of compound 6a as a yellow oil (Yield: 80.1%). Compound 6a was used in a subsequent process without a separate purification process.

$^1$H NMR (CDCl$_3$, 400 MHz) δ 3.99 (t, 2H), 3.60-3.57 (m, 2H), 2.90 (d, 2H), 2.66-2.62 (m, 1H), 2.11-2.06 (m, 1H), 1.59 (br, 1H), 1.44 (s, 9H), 0.46-0.42 (m, 2H), 0.32-0.28 (m, 2H)

Example 2

Preparation of tert-butyl 3-([([(9H-fluorene-9-yl)methoxy]carbonyl)(cyclopropyl) amino]methyl)azetidin-1-carboxylate (Formula 7a: X$^1$=Fmoc)

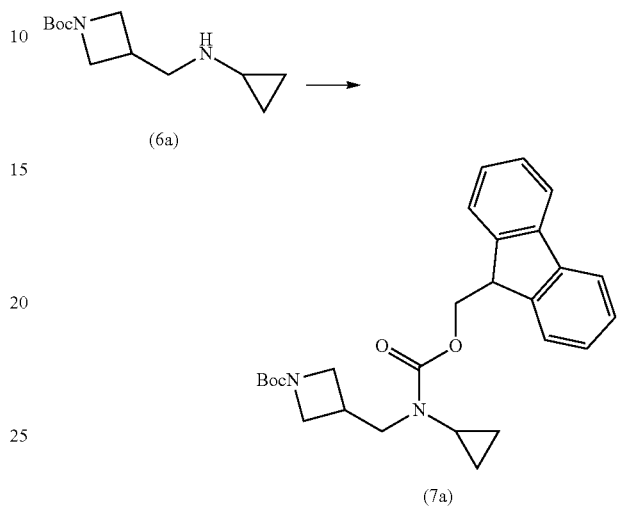

4.0 kg of dichloromethane was added into a reactor, 300.0 g of tert-butyl 3-[(cyclopropylamino)methyl]azetidin-1-carboxylate prepared in Example 1 and 188.4 g of diisopropylethylamine were sequentially added thereto, and then the reactor was cooled down to 0° C. 377.2 g of 9-fluorenylmethoxycarbonyl chloride was slowly added into the reactor such that the internal temperature of the reactor did not exceed 20° C., and the reaction mixture was stirred for 1 hour. 5.0 kg of water was added thereto to wash the organic layer, and the organic layer was further washed with 5.0 kg of a 1N hydrochloric acid aqueous solution. The organic layer was further washed with a 15% sodium chloride aqueous solution and treated with 250.0 g of anhydrous magnesium sulfate, filtered, and concentrated under reduced pressure, to thereby quantitatively yield 576.7 g of compound 7a as a yellow oil. Compound 7a was used in a subsequent process without a separate purification process.

$^1$H NMR (CDCl$_3$, 400 MHz) δ 7.72 (d, 2H), 7.56 (d, 2H), 7.36 (t, 2H), 7.30-7.26 (m, 2H), 4.52 (d, 2H), 4.17 (t, 1H), 3.89-3.85 (m, 2H), 3.56 (m, 2H), 3.30 (m, 2H), 2.60 (m, 1H), 2.28 (m, 1H), 1.43 (s, 9H), 0.61 (m, 2H), 0.45 (m, 2H)

Example 3

Preparation of tert-butyl 3-[(cyclopropyl-2,2,2-trifluoroacetamido)methyl] azetidin-1-carboxylate (Formula 7b: X$^1$=Tfa)

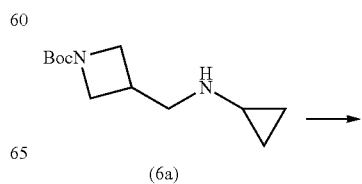

-continued

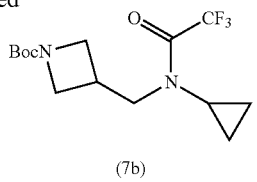

(7b)

2.7 kg of dichloromethane was added into a reactor, and 200.0 g of tert-butyl 3-[(cyclopropylamino)methyl]azetidin-1-carboxylate prepared in Example 1 was added thereto. 107.3 g of triethylamine was added thereto, and then the reactor was cooled down to 0° C. 222.7 g of trifluoroacetic acid anhydride was slowly added into the reactor such that the internal temperature of the reactor did not exceed 20° C., and the reaction mixture was stirred for 1 hour. 2.0 kg of water was added thereto to wash the organic layer, and the organic layer was further washed with 2.0 kg of a 1N hydrochloric acid aqueous solution. The organic layer was further washed with a 7% sodium chloride aqueous solution, treated with 100.0 g of anhydrous magnesium sulfate, filtered, and concentrated under reduced pressure, to thereby quantitatively yield 284.8 g of compound 7b as a white solid and yellow oil. Compound 7b was used in a subsequent process without a separate purification process.

$^1$H NMR (CDCl$_3$, 400 MHz) δ 3.99 (t, 2H), 3.60-3.57 (m, 2H), 2.90 (d, 2H), 2.68-2.60 (m, 1H), 2.10-2.06 (m, 1H), 1.44 (s, 9H), 0.46-0.41 (m, 2H), 0.32-0.28 (m, 2H)

Example 4

Preparation of tert-butyl 3-([cyclopropyl(4-methoxybenzyl)amino]methyl)azetidin-1-carboxylate (Formula 7c: X$^1$=PMB)

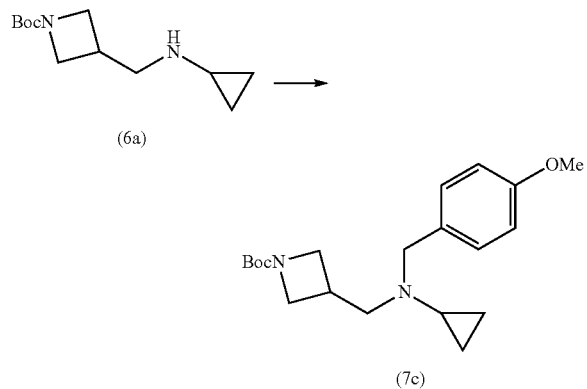

1.4 kg of acetonitrile was added into a reactor, 226.3 g of tert-butyl 3-[(cyclopropylamino)methyl]azetidin-1-carboxylate prepared in Example 1 and 111.3 g of triethylamine were sequentially added thereto, and then the reactor was cooled down to 0° C. 156.6 g of 4-methoxybenzyl chloride was slowly added thereto and stirred at ambient temperature overnight. The reaction mixture was concentrated under reduced pressure, and 2.0 kg of water and 1.8 kg of ethyl acetate (EA) were added thereto to separate the organic layer. The organic layer was further washed with 2.0 kg of a 0.5N hydrochloric acid aqueous solution.

The organic layer was further washed with a 7% sodium chloride aqueous solution, treated with 100.0 g of anhydrous magnesium sulfate, filtered, and then concentrated under reduced pressure, to thereby obtain 285.8 g of compound 7c as a yellow oil (Yield: 82.5%). Compound 7c was used in a subsequent process without a separate purification process.

$^1$H NMR (CDCl$_3$, 400 MHz) δ 7.17-7.13 (m, 2H), 6.85-6.82 (m, 2H), 3.88 (t, 2H), 3.80 (s, 3H), 3.65 (s, 2H), 3.47-3.43 (m, 2H), 2.78-2.72 (m, 1H), 2.66 (d, 2H), 1.72-1.67 (m, 1H), 1.41 (s, 9H), 0.51-0.47 (m, 2H), 0.37-0.34 (m, 2H)

Example 5

Preparation of (9H-fluorene-9-yl)methyl(azetidin-3-ylmethyl)(cyclopropyl)carbamate hydrochloride (Formula 2a: X$^1$=Fmoc, HA=HCl)

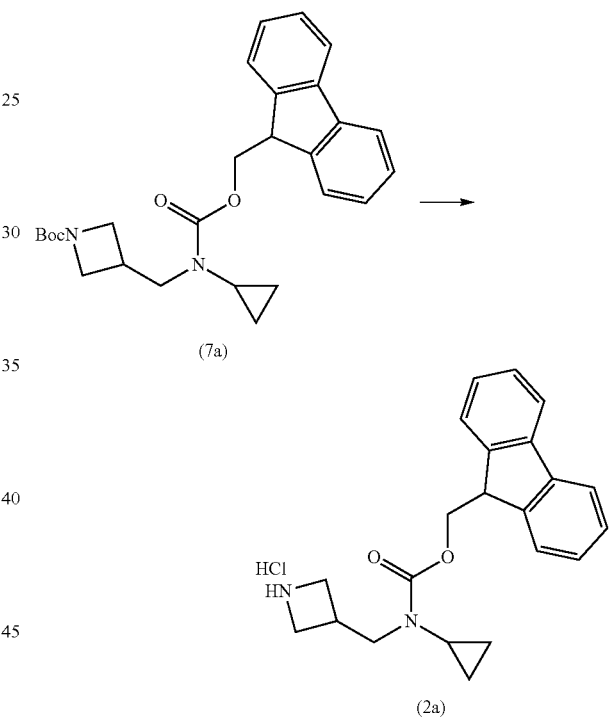

1.0 L of ethanol was added into a reactor, 100.0 g of tert-butyl 3-([([(9H-fluorene-9-yl)methoxy]carbonyl)(cyclopropyl)amino]methyl)azetidin-1-carboxylate prepared in Example 2 and 24.8 mL of concentrated hydrochloric acid were sequentially added thereto, and then the resultant mixture was heated. The reaction proceeded at reflux temperature for 30 minutes, and then the reaction mixture was concentrated under reduced pressure. 170 mL of ethyl acetate and 430 mL of n-hexane were added to the residue, stirred at ambient temperature overnight, filtered, and then dried at 40° C., to thereby yield 78.2 g of compound 2a (Yield: 91.2%).

$^1$H NMR (CDCl$_3$, 400 MHz) δ 9.63 (br, 1H), 9.40 (br, 1H), 7.75-7.70 (m, 2H), 7.60-7.55 (m, 2H), 7.38 (t, 2H), 7.32-7.29 (m, 2H), 4.52 (d, 2H), 4.18 (t, 1H), 3.99 (m, 2H), 3.81 (m, 2H), 3.44-3.28 (m, 2H), 2.94 (m, 1H), 2.27 (m, 1H), 0.60-0.59 (m, 2H), 0.43 (m, 2H)

Example 6

Preparation of N-(azetidin-3-ylmethyl)-N'-cyclopropyl-2,2,2-trifluoro acetamide hydrochloride (Formula 2b: $X^1$=Tfa, HA=HCl)

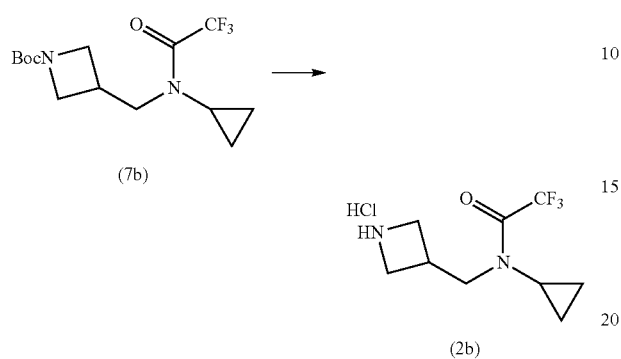

650 mL of methanol was added into a reactor, 64.5 g of tert-butyl 3-[(cyclopropyl-2,2,2-trifluoroacetamido)methyl]azetidin-1-carboxylate prepared in Example 3 and 22.0 mL of concentrated hydrochloric acid were sequentially added thereto, and then the resultant mixture was heated. The reaction proceeded at reflux temperature for 1 hour, and then the reaction mixture was concentrated under reduced pressure. 50 mL of isopropyl alcohol and 600 mL of ethyl acetate were added to the residue, stirred at ambient temperature overnight, filtered, and then dried at 40° C., to thereby yield 44.7 g of compound 2b (Yield: 86.3%).

$^1$H NMR (DMSO-$d_6$, 400 MHz) δ 9.39 (br, 2H), 3.98-3.93 (m, 2H), 3.77-3.72 (m, 2H), 3.67 (d, 2H), 3.09-3.01 (m, 1H), 2.96-2.90 (m, 1H), 0.88-0.86 (m, 4H)

Example 7

Preparation of N-(azetidin-3-ylmethyl)-N'-(4-methoxybenzyl)cyclopropanamine hydrochloride (Formula 2c: $X^1$=PMB, HA=HCl)

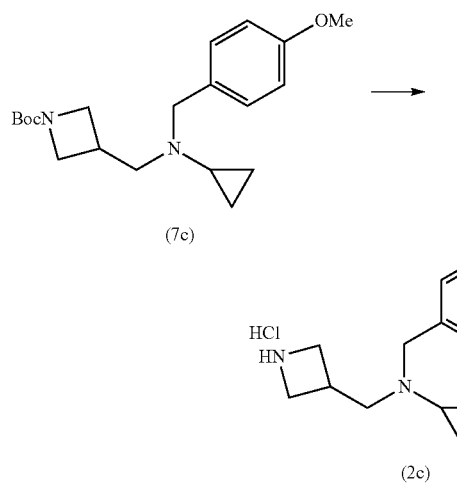

520 mL of isopropyl alcohol was added into a reactor, 52.0 g of tert-butyl 3-([cyclopropyl(4-methoxybenzyl) amino]methyl)azetidin-1-carboxylate prepared in Example 4 and 19.0 mL of concentrated hydrochloric acid were sequentially added thereto, and then the resultant mixture was heated. The reaction proceeded at reflux temperature for 6 hours, and then the reaction mixture was concentrated under reduced pressure. 85 mL of isopropyl alcohol and 210 mL of n-hexane were added to the residue, stirred at ambient temperature overnight, filtered, and then dried under vacuum, to thereby yield 34.0 g of compound 2c (Yield: 80.1%).

$^1$H NMR (CDCl$_3$, 400 MHz) δ 9.29-9.18 (m, 2H), 7.54 (m, 2H), 6.89-6.88 (m, 2H), 4.41 (m, 3H), 4.24 (m, 2H), 3.92 (m, 2H), 3.77 (m, 3H), 3.68 (m, 2H), 2.58 (m, 1H), 1.40-1.36 (m, 1H), 1.00 (m, 1H), 0.91 (m, 1H), 0.71 (m, 1H)

Example 8

Preparation of (9H-fluorene-9-yl)methylcyclopropyl ([1-(2-fluoro-5-[(4-oxo-3,4-dihydrophthalazin-1-yl)methyl]benzoyl)azetidin-3-yl]methyl)carbamate (Formula 4a: $X^1$=Fmoc)

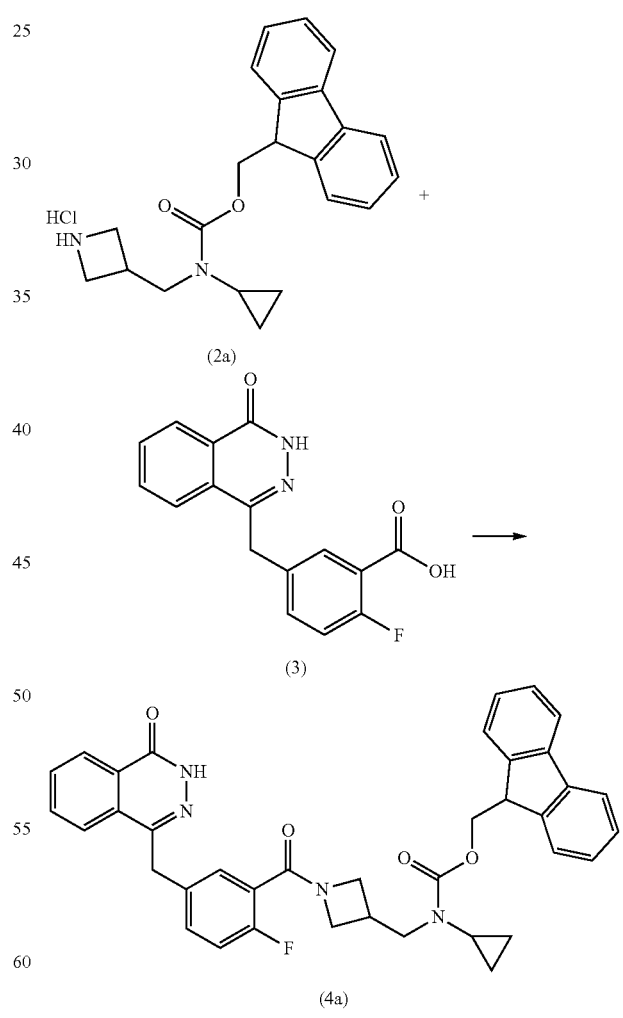

300 mL of dichloromethane was added into a reactor, and 29.8 g of 2-fluoro-5-[(4-oxo-3,4-dihydrophthalazin-1-yl)methyl]benzoic acid and 17.9 g of 1,1'-carbonyldiimidazole were sequentially added thereto. The reaction proceeded at ambient temperature for 1 hour, and then the reactor was cooled down to 15° C. Then, 42.3 g of (9H-fluorene-9-yl)methyl(azetidin-3-ylmethyl)(cyclopropyl)carbamate hydrochloride prepared in Example 5 was added thereto, and 19.4 g of diisopropylamine was slowly added thereto. The reaction mixture was stirred at ambient temperature for 1 hour, 300 mL of water was added thereto to wash the organic layer, and then the organic layer was further washed with a 1N hydrochloric acid aqueous solution and a 1N sodium carbonate aqueous solution. The organic layer was further washed with a 5% sodium chloride aqueous solution, treated with 10.0 g of anhydrous magnesium sulfate, filtered, and then concentrated under reduced pressure. 70 mL of ethyl acetate and 350 mL of n-hexane were added to the residue, stirred at ambient temperature overnight, filtered, and then dried at 50° C., to thereby yield 63.2 g of compound 4a (Yield: 91.3%).

$^1$H NMR (DMSO-$d_6$, 400 MHz) δ 12.60 (s, 1H), 8.26-8.24 (m, 1H), 7.97 (d, 1H), 7.90-7.78 (m, 4H), 7.65-7.62 (m, 2H), 7.48-7.28 (m, 7H), 4.51-4.48 (m, 2H), 4.32 (s, 2H), 4.26-4.23 (m, 1H), 3.97-3.86 (m, 2H), 3.62-3.56 (m, 2H), 3.30-3.25 (m, 2H), 2.24 (m, 1H), 1.24-1.23 (m, 1H), 0.48 (m, 2H), 0.38-0.35 (m, 2H)

Example 9

Preparation of N-cyclopropyl-2,2,2-trifluoro-N'-([1-(2-fluoro-5-[(4-oxo-3,4-dihydrophthalazin-1-yl)methyl]benzoyl)azetidin-3-yl]methyl)acetamide (Formula 4b: $X^1$=Tfa)

300 mL of dichloromethane was added into a reactor, and 29.8 g of 2-fluoro-5-[(4-oxo-3,4-dihydrophthalazin-1-yl)methyl]benzoic acid and then 17.9 g of 1,1'-carbonyldiimidazole were sequentially added thereto. The reaction proceeded at ambient temperature for 1 hour, the reactor was cooled down to 15° C., and then 28.5 g of N-(azetidin-3-ylmethyl)-N'-cyclopropyl-2,2,2-trifluoro acetamide hydrochloride prepared in Example 6, and then 19.4 g of triethylamine was slowly added thereto. After the reaction mixture was stirred at ambient temperature for 1 hour, 300 mL of water was added to wash the organic layer, and then the organic layer was further washed with a 1N hydrochloric acid aqueous solution and a 1N sodium carbonate aqueous solution. The organic layer was washed with a 5% sodium chloride aqueous solution, treated with 10.0 g of anhydrous magnesium sulfate, filtered, and then concentrated under reduced pressure. 400 mL of methanol was added to the residue, stirred at 0° C. for 2 hours, filtered, and then dried at 50° C., to thereby yield 44.7 g of compound 4b (Yield: 89.1%).

$^1$H NMR (DMSO-$d_6$, 400 MHz) δ 12.62 (s, 1H), 8.27-8.25 (m, 1H), 7.97 (d, 1H), 7.90-7.86 (m, 1H), 7.83-7.79 (m, 1H), 7.48-7.46 (m, 2H), 7.24-7.19 (m, 1H), 4.33 (s, 2H), 4.14-4.02 (m, 2H), 3.79-3.62 (m, 4H), 3.01-2.91 (m, 1H), 2.88-2.85 (m, 1H), 0.87-0.68 (m, 4H)

Example 10

Preparation of 4-(3-[3-([cyclopropyl(4-methoxybenzyl)amino]methyl)azetidin-1-carbonyl]-4-fluorobenzyl)phthalazin-1(2H)-one (Formula 4c: $X^1$=PMB)

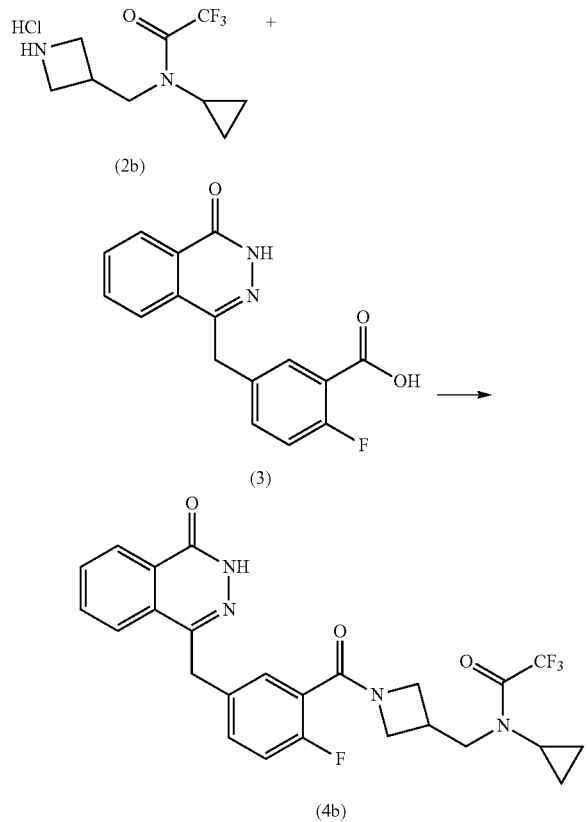

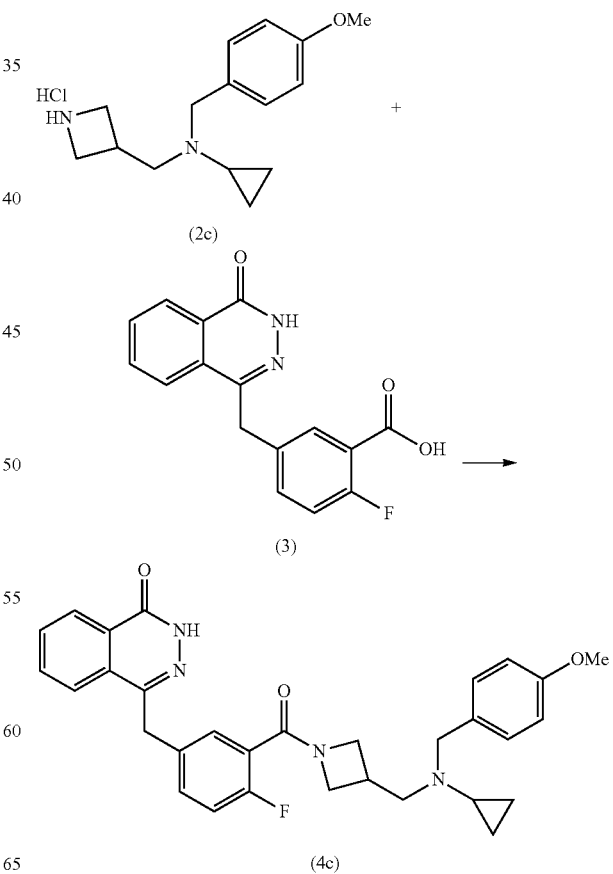

300 mL of dichloromethane was added into a reactor, and 29.8 g of 2-fluoro-5-[(4-oxo-3,4-dihydrophthalazin-1-yl)methyl]benzoic acid and 17.9 g of 1,1'-carbonyldiimidazole were sequentially added thereto. The reaction proceeded at ambient temperature for 1 hour, and then the reactor was cooled down to 15° C. Then, 31.1 g of N-(azetidin-3-ylmethyl)-N'-(4-methoxybenzyl)cyclopropanamine hydrochloride prepared in Example 7 was added thereto, and 19.4 g of triethylamine was slowly added thereto. The reaction mixture was stirred at ambient temperature for 1 hour, 300 mL of water was added thereto to wash the organic layer, and then the organic layer was washed with a 1N hydrochloric acid aqueous solution and a 1N sodium carbonate aqueous solution. The organic layer was washed with a 5% sodium chloride aqueous solution, treated with 10.0 g of anhydrous magnesium sulfate, filtered, and then concentrated under reduced pressure. 300 mL of toluene was added to the residue, stirred at ambient temperature overnight, filtered, and then dried at 50° C., to thereby yield 47.0 g of compound 4c (Yield: 81.2%).

$^1$H NMR (DMSO-d$_6$, 400 MHz) δ 12.61 (s, 1H), 8.26 (d, 1H), 7.98 (d, 1H), 7.92-7.87 (m, 1H), 7.84-7.80 (m, 1H), 7.52-7.48 (m, 2H), 7.43-7.42 (m, 1H), 7.26-7.12 (m, 2H), 6.97 (d, 2H), 4.32 (m, 2H), 4.26 (m, 2H), 4.18-4.09 (m, 2H), 3.90-3.82 (m, 2H), 3.77 (s, 3H), 3.36 (m, 1H), 3.32 (m, 2H), 2.55-2.50 (m, 1H), 1.19-1.13 (m, 1H), 0.86-0.85 (m, 1H), 0.80-0.75 (m, 1H), 0.69-0.68 (m, 1H)

Example 11

Preparation of 4-[3-(3-[(cyclopropylamino)methyl]azetidin-1-carbonyl)-4-fluorobenzyl]phthalazin-1(2H)-one (Formula 11 (1)

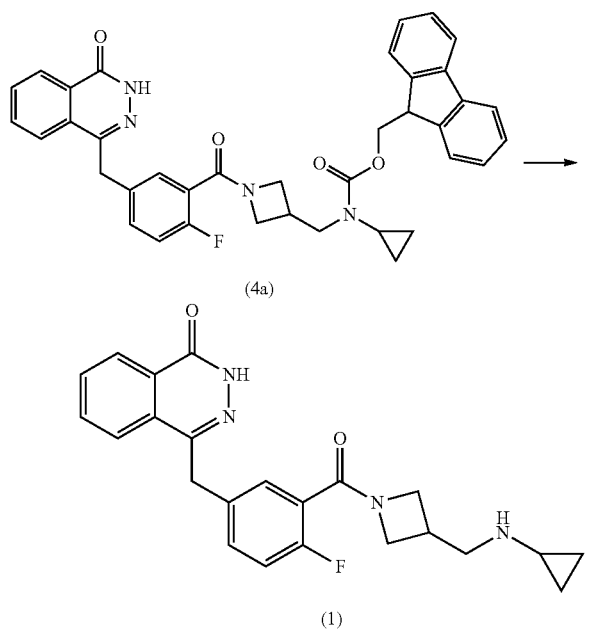

150 mL of acetonitrile was added into a reactor, and 30.0 g of (9H-fluorene-9-yl)methyl cyclopropyl([1-(2-fluoro-5-[(4-oxo-3,4-dihydrophthalazin-1-yl)methyl]benzoyl)azetidin-3-yl]methyl)carbamate prepared in Example 8 and 34.5 g of piperidine were sequentially added thereto and stirred at ambient temperature for 1 hour. After the reaction mixture was concentrated under reduced pressure, 300 mL of a 2N hydrochloric acid aqueous solution was added to the residue, stirred for 1 hour, and then filtered through diatomaceous earth. Then, the filtrate was adjusted to pH 9 or greater with a 1N sodium hydroxide solution and extracted by adding 300 mL of dichloromethane. The aqueous layer was further extracted by adding 300 mL of dichloromethane thereto, and then the organic layer was mixed therewith, washed with a 5% sodium chloride aqueous solution, and then concentrated. 80 mL of methanol and 40 mL of dichloromethane were added to the residue, and then 150 mL of acetone was slowly added thereto. The resulting solid was stirred at ambient temperature overnight, filtered, and dried at 40° C. to yield 17.5 g of compound 1 (Yield: 90.1%).

$^1$H NMR (DMSO-d$_6$, 400 MHz) δ 12.62 (s, 1H), 8.27-8.25 (m, 1H), 7.97 (d, 1H), 7.90-7.86 (m, 1H), 7.84-7.79 (m, 1H), 7.46-7.43 (m, 2H), 7.22-7.18 (m, 1H), 4.32 (s, 2H), 4.04-3.56 (m, 4H), 2.73-2.63 (m, 3H), 2.30 (br, 1H), 2.00-1.95 (m, 1H), 0.33-0.12 (m, 4H)

Example 12

Preparation of 4-[3-(3-[(cyclopropylamino)methyl]azetidin-1-carbonyl)-4-fluorobenzyl]phthalazin-1(2H)-one Formula 1)(2)

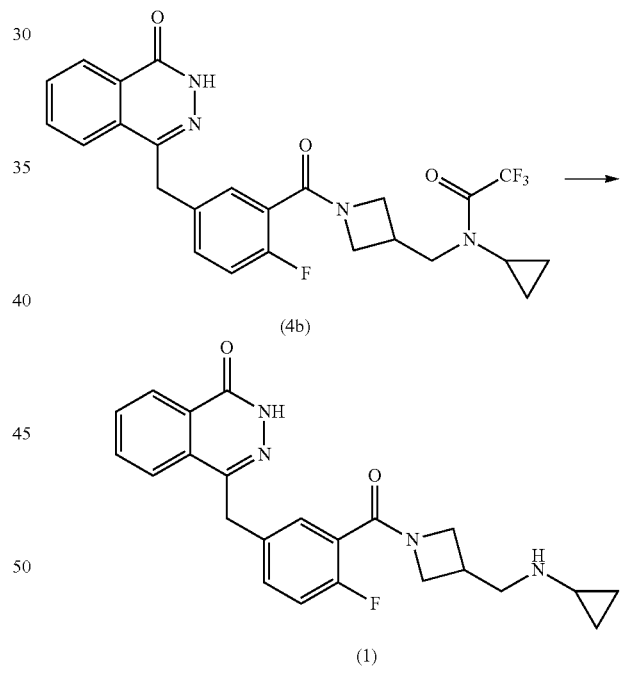

300 mL of methanol was added into a reactor, 30.0 g of N cyclopropyl-2,2,2-trifluoro-N'-([1-(2-fluoro-5-[(4-oxo-3,4-dihydrophthalazin-1-yl)methyl]benzoyl)azetidin-3-yl]methyl)acetamide prepared in Example 9, and then the reactor was cooled down to 0° C. 60 mL of a 20% potassium carbonate aqueous solution was slowly added into the reactor such that the internal temperature of the reactor did not exceed 20° C., and the reaction mixture was stirred at ambient temperature overnight. 240 mL of water and 300 mL of dichloromethane 300 mL were added thereto to extract the aqueous layer, and then the aqueous layer was further extracted with 300 mL of dichloromethane. Then, the organic layer was mixed therewith, washed with a 5% sodium chloride aqueous solution, and then concentrated. 100 mL of methanol and 50 mL of dichloromethane were added to the residue, and then 200 mL of acetone was slowly added thereto. The resulting solid was stirred at ambient temperature overnight, filtered, and dried at 40° C., to thereby yield 22.4 g of compound 1 (Yield: 92.1%).

$^1$H NMR (DMSO-$d_6$, 400 MHz) δ 12.59 (5, 1H), 8.27-8.25 (m, 1H), 7.97 (d, 1H), 7.91-7.87 (m, 1H), 7.84-7.80 (m, 1H), 7.46-7.42 (m, 2H), 7.22-7.18 (m, 1H), 4.32 (s, 2H), 4.04-3.55 (m, 4H), 2.74-2.63 (m, 3H), 2.30 (br, 1H), 2.02-1.97 (m, 1H), 0.34-0.14 (m, 4H)

Example 13

Preparation of 4-[3-(3-[(cyclopropylamino)methyl] azetidin-1-carbonyl)-4-fluorobenzyl]phthalazin-1 (2H)-one (Formula 1) (3)

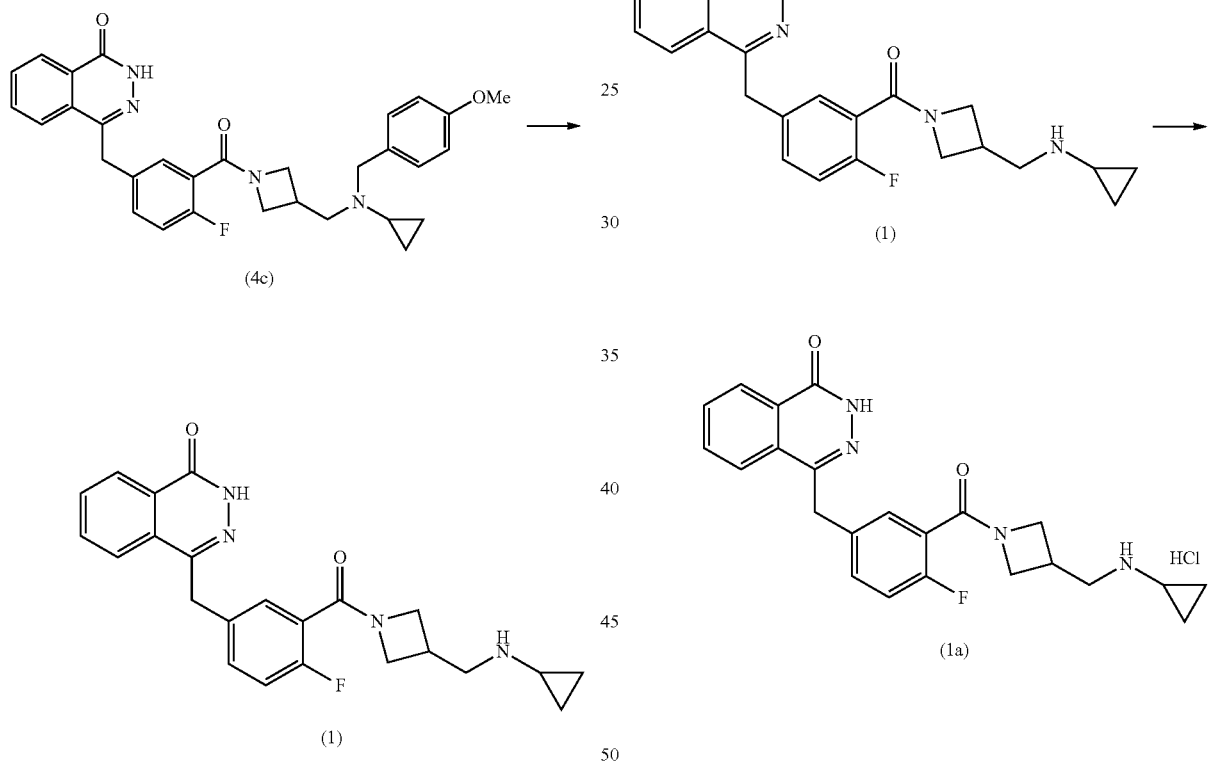

100 mL of trifluoroacetic acid was added into a reactor, and 10.0 g of 4-(3-[3-([cyclopropyl(4-methoxybenzyl) amino]methyl)azetidin-1-carbonyl]-4-fluorobenzyl)phthalazin-1(2H)-one prepared in Example 10 was added thereto and stirred at 60° C. for 1 hour. The reactor was then cooled down to 0° C., 100 mL of dichloromethane 100 mL was added thereto, and then 100 mL of water was slowly added thereto. The aqueous layer was further washed with 100 mL of dichloromethane, adjusted to pH 9 or greater with a 1N sodium hydroxide aqueous solution, and then extracted with 100 mL of dichloromethane. The aqueous layer was further extracted with 100 mL of dichloromethane, and the organic layer was mixed therewith, washed with a 5% sodium chloride aqueous solution and then concentrated. 60 mL of methanol and 30 mL of dichloromethane were added to the residue, and 120 mL of acetone was slowly added thereto. The resulting solid was stirred at ambient temperature overnight, filtered, and dried at 40° C., to thereby yield 13.4 g of compound 1 (Yield: 86.9%).

$^1$H NMR (DMSO-$d_6$, 400 MHz) δ 12.59 (s, 1H), 8.27-8.25 (m, 1H), 7.98 (d, 1H), 7.91-7.87 (m, 1H), 7.85-7.80 (m, 1H), 7.46-7.42 (m, 2H), 7.23-7.18 (m, 1H), 4.32 (s, 2H), 4.04-3.55 (m, 4H), 2.74-2.63 (m, 3H), 2.30 (br, 1H), 2.02-1.97 (m, 1H), 0.34-0.14 (m, 4H)

Example 14

Preparation of hydrochloride salt of 4-[3-(3-[(cyclopropylamino)methyl]azetidin-1-carbonyl)-4-fluorobenzyl]phthalazin-1(2H)-one (Formula 1a) (1)

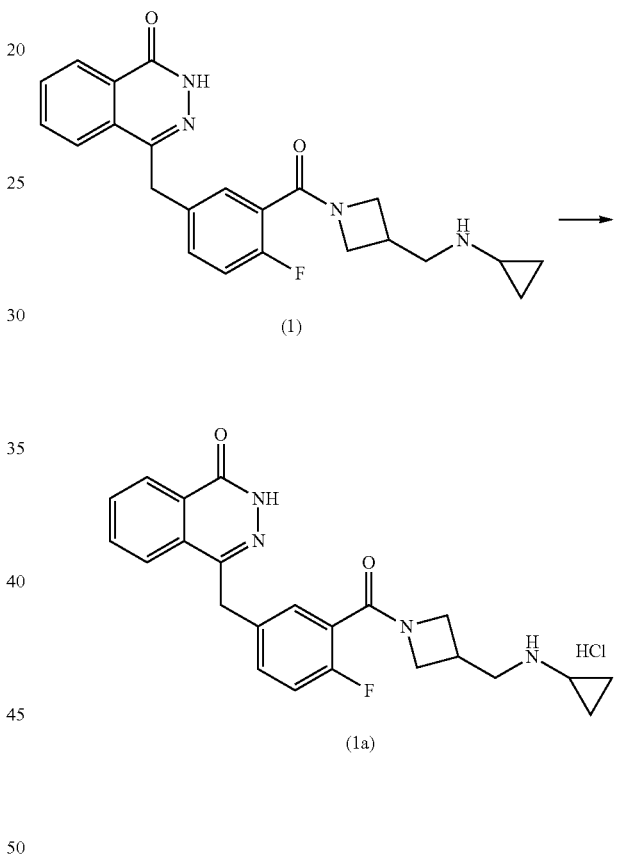

40 mL of methanol and 100 mL of acetone were added into a reactor, 10.0 g of 4-[3-(3-[(cyclopropylamino)methyl] azetidin-1-carbonyl)-4-fluorobenzyl]phthalazin-1(2H)-one prepared in Example 11 was added thereto, and then the reactor was cooled down to 0° C. 2.4 g of concentrated hydrochloric acid was slowly added thereto over 30 minutes, stirred at ambient temperature overnight, filtered, and dried at 40° C., to thereby yield 10.4 g of compound 1 a (Yield: 95.7% and HPLC purity: 99.86% [area %]).

$^1$H NMR (DMSO-$d_6$, 400 MHz) δ 12.61 (s, 1H), 9.37 (br, 2H), 8.27-8.25 (m, 1H), 7.98 (d 1H), 7.93-7.88 (m, 1H), 7.85-7.81 (m, 1H), 7.49-7.45 (m, 2H), 7.25-7.20 (m, 1H), 4.33 (s, 2H), 4.13-3.82 (m, 4H), 3.31-3.22 (m, 2H), 3.07-3.00 (m, 1H), 2.65-2.60 (m, 1H), 0.91-0.67 (m, 4H)

Example 15

Preparation of hydrochloride salt of 4-[3-(3-[(cyclopropylamino)methyl]azetidin-1-carbonyl)-4-fluorobenzyl]phthalazin-1(2H)-one (Formula 1a) (2)

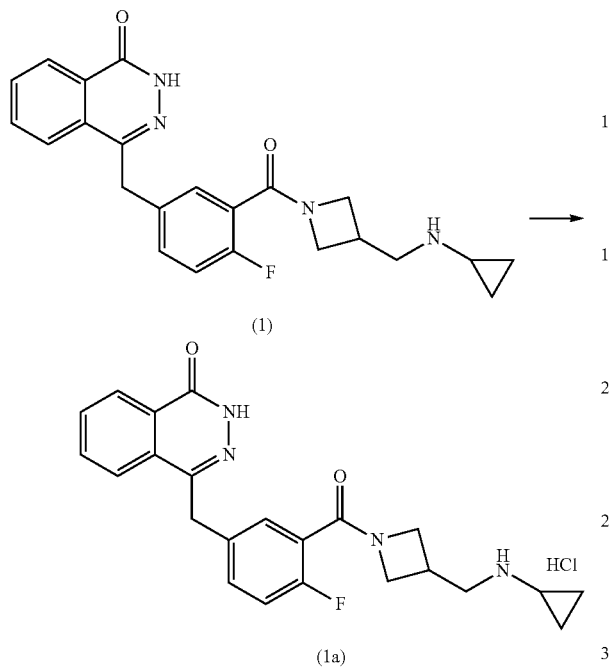

40 mL of ethanol and 60 mL of ethyl acetate were added into a reactor, 10.0 g of 4-[3-(3-[(cyclopropylamino)methyl]azetidin-1-carbonyl)-4-fluorobenzyl]phthalazin-1(2H)-one prepared in Example 12 was added thereto, and then the reactor was cooled down to 0° C. 2.4 g of concentrated hydrochloric acid was slowly added thereto over 30 minutes, stirred at ambient temperature overnight, filtered, and dried at 40° C., to yield 10.4 g of compound 1a (Yield: 92.1% and HPLC purity: 99.86% [area %]).

$^1$H NMR (DMSO-$d_6$, 400 MHz) δ 12.60 (s, 1H), 9.19 (br, 2H), 8.27-8.25 (m, 1H), 7.98 (d, 1H), 7.93-7.89 (m, 1H), 7.85-7.81 (m, 1H), 7.50-7.44 (m, 2H), 7.25-7.20 (m, 1H), 4.33 (s, 2H), 4.13-3.81 (m, 4H), 3.30-3.22 (m, 2H), 3.05-2.98 (m, 1H), 2.65-2.61 (m, 1H), 0.88-0.68 (m, 4H)

Example 16

Preparation of hydrochloride salt of 4-[3-(3-[(cyclopropylamino)methyl]azetidin-1-carbonyl)-4-fluorobenzyl]phthalazin-1(2H)-one (Formula 1a) (3)

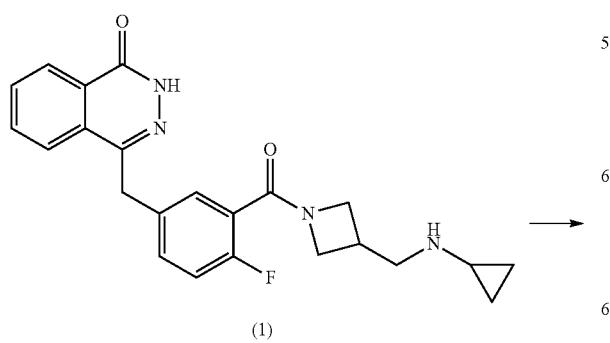

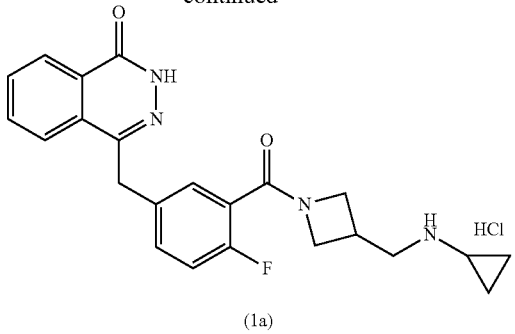

50 mL of ethanol and 100 mL of tert-butylmethylether were added into a reactor, 10.0 g of 4-[3-(3-[(cyclopropylamino)methyl]azetidin-1-carbonyl)-4-fluorobenzyl]phthalazin-1(2H)-one prepared in Example 13 was added thereto, and then the reactor was cooled down to 0° C. 2.4 g of concentrated hydrochloric acid was slowly added thereto over 30 minutes, stirred at ambient temperature overnight, filtered, and dried at 40° C., to yield 10.6 g of compound 1 a (Yield: 97.2% and HPLC purity: 99.80% [area %]).

$^1$H NMR (DMSO-$d_6$, 400 MHz) δ 12.60 (s, 1H), 9.23 (br, 2H), 8.27-8.25 (m, 1H), 7.98 (d, 1H), 7.93-7.89 (m, 1H), 7.85-7.81 (m, 1H), 7.50-7.44 (m, 2H), 7.25-7.20 (m, 1H), 4.33 (s, 2H), 4.13-3.81 (m, 4H), 3.28-3.22 (m, 2H), 3.08-2.97 (m, 1H), 2.66-2.62 (m, 1H), 0.89-0.68 (m, 4H)

The described embodiments are to be considered in all respects only as illustrative and not restrictive. Those of ordinary skill in the art will recognize that the present invention may be embodied in other specific forms without departing from its spirit or essential characteristics. The scope of the present invention is, therefore, indicated by the appended claims rather than by the foregoing description. All changes which come within the meaning and range of equivalency of the claims are to be embraced within the scope of the present invention.

The invention claimed is:

1. A method of preparing a compound of Formula 1, or a pharmaceutically acceptable salt thereof,

[Formula 1]

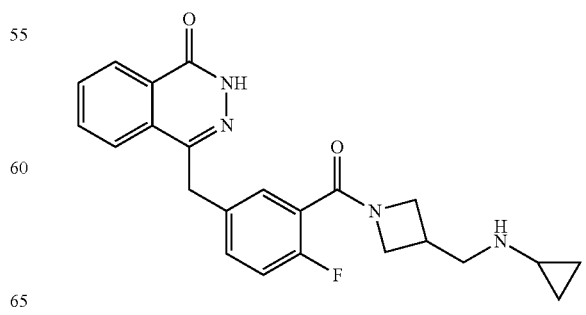

comprising:

preparing a compound of Formula 4,

[Formula 4]

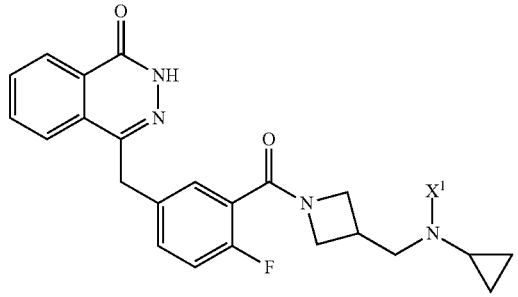

wherein X¹ is an amine protecting group selected from the group consisting of fluorenylmethoxycarbonyl (Fmoc), trifluoroacetyl (Tfa), and p-methoxybenzyl (PMB), wherein the compound of Formula 4 is prepared by reacting a compound of Formula 2

[Formula 2]

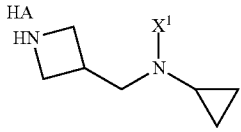

wherein X¹ is an amine protecting group selected from the group consisting of fluorenylmethoxycarbonyl (Fmoc), trifluoroacetyl (Tfa), and p-methoxybenzyl (PMB), and HA is an acid which forms an acid addition salt with a compound of Formula 3:

[Formula 3]

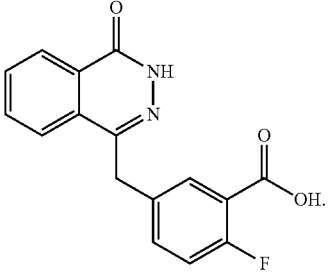

wherein preparing the compound of Formula 4 is carried out in the presence of at least one amide coupling reagent and at least one base, and wherein the at least one amide coupling reagent is selected from the group consisting of, 1,1'-carbonyl-diimidazole, N-(3-dimethylaminopropyl)-N'-ethylcarbodiimide hydrochloride(EDC), and any combination thereof, and the at least one base is, triethylamine, and deprotecting the compound of Formula 4.

2. The method of claim 1, wherein HA is hydrochloric acid (HCl), hydrobromic acid (HBr), or hydroiodic acid (HI).

3. The method of claim 1, wherein X¹ is an amine protecting group selected from the group consisting of fluorenylmethoxycarbonyl (Fmoc) and p-methoxybenzyl (PMB).

4. The method of claim 1, comprising reacting the compound of Formula 4 with a non-nucleophilic base, wherein X¹ in Formula 4 is fluorenylmethoxycarbonyl (Fmoc).

5. The method of claim 1, comprising reacting the compound of Formula 4 with an alkali base, wherein X¹ in Formula 4 is trifluoroacetyl (Tfa).

6. The method of claim 1, comprising reacting the compound of Formula 4 with an acid, wherein X¹ in Formula 4 is p-methoxybenzyl (PMB).

7. The method of claim 1, further comprising reacting the compound of Formula 1 with an acid to prepare a pharmaceutically acceptable acid addition salt of the compound of Formula 1.

8. The method of claim 1, wherein the at least one amide coupling reagent is selected from the group consisting of trimethylacetyl chloride, 1,1'-carbonyldiimidazole, and any combination thereof.

* * * * *